United States Patent
Yoon et al.

(10) Patent No.: US 10,265,354 B2
(45) Date of Patent: Apr. 23, 2019

(54) ENTEROPATHOGENIC E. COLI BACTERIOPHAGE ESC-CHP-2 AND USE THEREOF FOR INHIBITING PROLIFERATION OF ENTEROPATHOGENIC E. COLI

(71) Applicant: Intron Biotechnology, Inc., Gyeonggi-do (KR)

(72) Inventors: Seong Jun Yoon, Seoul (KR); Sang Hyeon Kang, Seoul (KR); Soo Youn Jun, Seoul (KR); Hyoun Rok Paik, Incheon (KR); Jee Soo Son, Seoul (KR); Byung Kuk Kim, Gyeonggi-do (KR); Hee Jeong Shin, Gyeonggi-do (KR)

(73) Assignee: INTRON BIOTECHNOLOGY, INC., Gyeonggi-Do (KR)

( * ) Notice: Subject to any disclaimer, the term of this patent is extended or adjusted under 35 U.S.C. 154(b) by 0 days.

(21) Appl. No.: 15/538,551

(22) PCT Filed: Dec. 28, 2015

(86) PCT No.: PCT/KR2015/014330
§ 371 (c)(1),
(2) Date: Jun. 21, 2017

(87) PCT Pub. No.: WO2016/108540
PCT Pub. Date: Jul. 7, 2016

(65) Prior Publication Data
US 2017/0348365 A1    Dec. 7, 2017

(30) Foreign Application Priority Data
Dec. 30, 2014   (KR) .................. 10-2014-0192982

(51) Int. Cl.
| | |
|---|---|
| C12N 7/00 | (2006.01) |
| A61K 35/76 | (2015.01) |
| A23L 2/38 | (2006.01) |
| A23K 20/195 | (2016.01) |
| A23K 10/16 | (2016.01) |
| A01N 63/00 | (2006.01) |
| A61K 9/00 | (2006.01) |
| A61L 2/18 | (2006.01) |
| C02F 3/34 | (2006.01) |
| A23L 2/52 | (2006.01) |
| A23K 10/18 | (2016.01) |
| A23K 50/30 | (2016.01) |
| A23K 10/00 | (2016.01) |

(52) U.S. Cl.
CPC ............ *A61K 35/76* (2013.01); *A01N 63/00* (2013.01); *A23K 10/00* (2016.05); *A23K 10/16* (2016.05); *A23K 10/18* (2016.05); *A23K 20/195* (2016.05); *A23K 50/30* (2016.05); *A23L 2/38* (2013.01); *A23L 2/52* (2013.01); *A61K 9/0053* (2013.01); *A61K 9/0095* (2013.01); *A61L 2/18* (2013.01); *C02F 3/34* (2013.01); *C12N 7/00* (2013.01); *C02F 2303/04* (2013.01); *C12N 2795/10121* (2013.01); *C12N 2795/10131* (2013.01); *C12N 2795/10132* (2013.01)

(58) Field of Classification Search
None
See application file for complete search history.

(56) References Cited

U.S. PATENT DOCUMENTS

| | | | | |
|---|---|---|---|---|
| 9,358,258 | B2 * | 6/2016 | Kim | A61K 35/76 |
| 9,950,015 | B2 * | 4/2018 | Cimino | A61K 35/35 |
| 9,950,018 | B2 * | 4/2018 | Shin | A61K 35/76 |
| 10,028,984 | B2 * | 7/2018 | Yoon | A23K 20/195 |
| 2014/0017205 | A1 * | 1/2014 | Shin | C12N 7/00 424/93.6 |
| 2014/0356330 | A1 * | 12/2014 | Kim | A61K 35/76 424/93.6 |
| 2015/0322409 | A1 * | 11/2015 | Yoon | C12N 7/00 424/93.6 |
| 2017/0035817 | A1 * | 2/2017 | Shin | A23K 20/195 |
| 2017/0037380 | A1 * | 2/2017 | Shin | A23K 20/10 |
| 2017/0037382 | A1 * | 2/2017 | Shin | A23K 10/18 |
| 2017/0333498 | A1 * | 11/2017 | Yoon | A61K 35/76 |
| 2017/0333499 | A1 * | 11/2017 | Yoon | A23L 2/38 |
| 2017/0340686 | A1 * | 11/2017 | Yoon | A61K 35/76 |
| 2017/0348365 | A1 * | 12/2017 | Yoon | A23L 2/38 |
| 2017/0368116 | A1 * | 12/2017 | Regeimbal | A61K 35/76 |

(Continued)

FOREIGN PATENT DOCUMENTS

| | | |
|---|---|---|
| JP | 2004514443 | 5/2004 |
| KR | 20100116289 | 11/2010 |

(Continued)

OTHER PUBLICATIONS

Clements et al, Gut Microbes 3:2, 71-87, Mar./Apr. 2012. (Year: 2012).*

(Continued)

*Primary Examiner* — Nita M. Minnifield
(74) *Attorney, Agent, or Firm* — Ballard Spahr LLP

(57) ABSTRACT

The present invention relates to a Myoviridae bacteriophage Esc-CHP-2 that is isolated from the nature and can kill specifically enteropathogenic *E. coli* strains, which has a genome represented by the nucleotide sequence of SEQ. ID. NO: 1 (Accession NO: KCTC 12661BP), and a method for preventing and treating the infections of enteropathogenic *E. coli* using the composition comprising said bacteriophage as an active ingredient.

2 Claims, 1 Drawing Sheet
Specification includes a Sequence Listing.

(56) References Cited

U.S. PATENT DOCUMENTS

| | | | |
|---|---|---|---|
| 2017/0369852 A1* | 12/2017 | Yoon | C12N 7/00 |
| 2018/0000125 A1* | 1/2018 | Yoon | A61K 35/76 |
| 2018/0092386 A1* | 4/2018 | Lu | A23L 3/3463 |
| 2018/0119109 A1* | 5/2018 | Yoon | C12N 7/00 |

FOREIGN PATENT DOCUMENTS

| | | | | |
|---|---|---|---|---|
| KR | 20110041670 | | 4/2011 | |
| WO | WO-2013073843 A1 * | | 5/2013 | A61K 35/76 |
| WO | WO-2016108536 A1 * | | 7/2016 | A23K 20/195 |
| WO | WO-2016108538 A1 * | | 7/2016 | A61K 35/76 |
| WO | WO-2016108540 A1 * | | 7/2016 | A23L 2/38 |
| WO | WO-2016108541 A1 * | | 7/2016 | A61K 35/76 |
| WO | WO-2016108542 A1 * | | 7/2016 | A23L 2/38 |
| WO | WO-2016114517 A1 * | | 7/2016 | A61K 35/76 |
| WO | WO-2017111306 A1 * | | 6/2017 | A61Q 19/10 |
| WO | WO-2018101594 A1 * | | 6/2018 | |

OTHER PUBLICATIONS

Yang et al, Arch. Microbiol., (2017), 199:811-825. published online:Jun. 9, 2017 (Year: 2017).*
Tonnat et al, Food Research International 66 (2014) 23-28. available online Sep. 6, 2014 (Year: 2014).*
Gohar et al, BMC Res Notes. (2016) 9:80, 18 pages. (Year: 2016).*
Saeedi et al, Microbial Pathogenesis 103 (2017) 186e195. available online Jan. 3, 2017 (Year: 2017).*
Mani et al, Vaccine 34 (2016) 2887-2894. available online Mar. 12, 2016 (Year: 2016).*
Allocati et al. Int. J. Environ,Res. Public Health, 2013, 10, 6235-6254. published Nov. 25, 2013 (Year: 2013).*
Gerdts et al, ILAR Journal, 2015, 56/1:53-62 (Year: 2015).*
Walker et al, Vaccine, 2015, 33:954-965. available online:Dec. 5, 2014 (Year: 2015).*
Wenzel et al, Vaccine, 2017, 35:6798-6802. available online: Sep. 7, 2017 (Year: 2017).*
Tomat, D. et al., "Phage Biocontrol of Enteropathogenic and Shiga Toxin-producing *Escherichia coli* during Milk Fermentation", Letters in Applied Microbiology, (2013), 57, 1: 3-10, See abstract; and pp. 4-7.
International Search Report and Written Opinion dated May 4, 2016 by the International Searching Authority for International Application No. PCT/KR2015/014330, which was filed on Dec. 28, 2015 and published as WO 2016/108540 on Jul. 7, 2016 (Applicant-Intron Biotechnology Inc.) (Original—8 pages/Translated—2 pages.
Branko, V. et al., Recent Advances in Understanding the Virulence of Enterohemorrhagic *Escherichia coli* in Food. Inst Meat Hygiene Technol. 2011; 52(1):52-9 (Abstract Only).

Cordonnier, C. et al., Probiotic and Enterohemorrhagic *Escherichia coli*: An Effective Strategy Against a Deadly Enemy? Critical Rev Microbiol. 2017; 43(1):116-32.
Enterohemorrhagic *Escherichia coli*. Johns Hopkins Medicine Health Library. 2018. Retrieved from the Internet: https://www.hopkinsmedicine.org/healthlibrary/test_procedures/urology/enterohemorrhagic_escherichia_coli_85,P01430 [retrieved on May 25, 2018] (3 pages).
Ho, N.K. et al., Enterhemorrhagic *Escherichia coli* O157:H7 Shiga Toxins Inhibit Gamma Interferon-Mediated Cellular Activation. Infect Immun. 2012; 80(7):2307-15.
Laing, C.R. et al., A Comparison of Shiga-Toxin 2 Bacteriophage from Classical Enterohemorrhagic *Escherichia coli* Serotypes and the German *E. coli* O104:H4 Outbreak Strain. PLoS One. 2012; 7(5):e37362 (12 pages).
Los, J.M. et al., Bacteriophages Carrying Shiga Toxin Genes: Genomic Variations, Detection and Potential Treatment of Pathogenic Bacteria. Future Microbiol. 2011; 6(8):909-24.
Los, J.M. et al., Enterohemorrhagic Strains of *Escherichia coli* (EHEC) and Shiga Toxin-Encoding Bacteriophages. Postepy Mikrobiologi. 2011; 50(3):175-90 (Abstract only).
NCBI, GenBank Accession No. EF460875.1. Enterobacteria Phage phiEcoM-GJ1, Complete Genome. 2008 (24 pages).
NCBI, GenBank Accession No. HQ259103.1, *Salmonella* Phage SFP10, Complete Genome. 2011 (78 pages).
Orth, D. et al., Prevention and Treatment of Enterohemorrhagic *Escherichia coli* Infections in Humans. Exper Rev Anti Ther. 2008; 6(1):101-8.
Pacheco, A.R. et al., Shiga Toxin in Enterohemorrhagic *E.coli*: Regulation and Novel Anti-Virulence Strategies. Front Cell Infect Microbiol. 2012; 2(81):1-12.
Rojas-Lopez, M. et al., Intestinal Pathogenic *Escherichia coli*: Insights for Vaccine Development. Front Microbiol. 2018; 9:440 (17 pages).
Viazis, S. et al., Reduction of *Escherichia coli* O157:H7 Viability on Hard Surfaces by treatment with a Bacteriophage Mixture. Int J Food Microbiol. 2011; 145(1):37-42.
Walker, R.I., An Assessment of Enterotoxigenic *Escherichia coli* and *Shigella* Vaccine Candidates for Infants and Children. Vaccine. 2015; 33:954-65.
International Search Report and Written Opinion dated May 4, 2016 by the International Searching Authority for Patent Application No. PCT/KR/014328, which was filed on Dec. 28, 2015 and published as WO 2016/108538 dated Jul. 7, 2016 (Inventor—Yoon et al.; Applicant—Intron Biotechnology, Inc.) (Original—8 pages; Translation—7 pages).
Non-Final Office Action dated Jun. 1, 2018 by the U.S. Patent and Trademark Office for U.S. Appl. No. 15/538,538, filed Jun. 21, 2017 and published as US 2017/0333498 on Nov. 23, 2017 (Inventor—Yoon et al.; Applicant—Intron Biotechnology, Inc.) (15 pages).

\* cited by examiner

SEQUENCE LISTING

```
<160> NUMBER OF SEQ ID NOS: 1

<210> SEQ ID NO 1
<211> LENGTH: 53363
<212> TYPE: DNA
<213> ORGANISM: Bacteriophage Esc-CHP-2

<400> SEQUENCE: 1
tttgcaattt caccaagttc tttcgccttg tacagcatga tgccagtacg agctatggtg      60
cattctgcaa tcatttcgcc agagtcacgt aaacgacggg tcgttaaagt agccttgtcg     120
ttcaacaaaa ctacttcatt cacggtatct tcgtcgttaa gctgaaccag gttttggttt     180
tgcttcactt gcgttaccct tttggatgtt aggaggatta ggatttggtt tgccaaggtc     240
acaagttccg aacacgcccg aatggaacat gacttcgttt gcaacttcgg tagtgatagt     300
accgttgtta accagcaggt caacagcaaa tgccaaatct ttagctcgct tcgctttctc     360
aacattggat tcagggaaga tatctaacca ttcgtagtta tattcttcaa tgccaaagtg     420
cgcttggaca atcttgtcta ccacatctaa acgagggtcg aacacagaag tctgcaagcc     480
agtcaacaag tcgatatagt ttacgaggtc agattcgccc gtagcattca taccgtctgg     540
agatgcagaa aggaaacgtg tagccggaat accaactgcg gcagcaacta tcttcaagta     600
ttcccaaatc aaatctttta caccagacag tgcgattgat ttggtgtcat atttctcagt     660
attgtcgaga attaagacgt tataaatact ctttgccagc ttcataagtt tgaagcgctt     720
catcacagca gcttcacctt ccggtgatgt aagcagggat tgtaagcctt caacagttac     780
cacatcaatg gtggcttctt gggcaaggct ggcagcagca gcagcagttg tatagaactg     840
gtcaatcgtt ttcagcagtg gaataagtac cgaatcagaa taccacatgt tacgttggaa     900
ttcgaacagt ggcagttcag taccctcgaa ccgaaggaaa cgagtgtaat ggatatagcc     960
aggataccca gccaaagtgt aatactctgg caaaccatag tgaggactca aagggtccga    1020
aaccatagtc cctgcggcaa ataagcgtga gcggtcaata actctcatgg atttaataca    1080
tccagtcttc aagttatcca gtcgtaatgg tgtatcaagt ttgcccgtgc cttttaggtc    1140
gagcagaaca aatgaagtcc catacaatct ggcccattga tatgcttcac ggaacagctt    1200
acgaatacga agtttcttat ccgctttgcg tccttcttca ctatcaatat gtcgccactt    1260
acgcgtcata tcttgaggaa taacggtaca cactttctgt gccacccaat cctcacggaa    1320
gcggttcata agttcgcggt aattcgcgtt cttgtttgag aaagtccact ggttaaaagt    1380
ggacttatct gcctgaccgc ccaaccccgt tacaaggttt tctaacccat ctgcaacttt    1440
aacagaaaga ttgtttttct tcttggaagt cattatttct tccttagaat agttccatta    1500
cccttaacaa tttgaatgtt gtcggaggtg tggagtcgca gatttgactc gtgctttaac    1560
ttaacacagt cgctctctgt ggtagaaact gcctcaatca cacacaaaat gtttccttcc    1620
aaatcttgaa tctggaagga attgttcttg cgtgagcggg catctaatcg agtgataacc    1680
gccatatttt acatccatgc ggagtagttg gcacttgggc cagagaattc gattgcaacc    1740
```

-continued

| | | | | |
|---|---|---|---|---|
| atatctgaaa | cgttatcgac | acaatcgtcg | tgtccagtac | cactacccaa agaagtgaat 1800 |
| ccaagtattt | cacgtctaac | gtggtcaatg | tgttcatgac | cagcagggaa gaatattctc 1860 |
| ttttgcgaga | aatatgggat | tgcgttaagg | aatcgagtta | ccttgtcatt accattgatg 1920 |
| ccatcacgag | gcagcggtaa | aactcggaca | ctcccatctc | taataaattg ttggttcaag 1980 |
| aattgtccgg | cagacttgtc | ttccatgtac | aatgcacgag | gaatacaacc tacacatttc 2040 |
| aagtccaact | tgttgcattt | gttccagaag | tcgataatag | cagtcttgag ttctggagtt 2100 |
| tcaaacttac | cgagcataat | atctaaacaa | taaacatcac | gctctttagt cacgccccaa 2160 |
| tgcttaagga | ccgaataatc | agaataagat | ttggcagttg | atgccgtatc cgctgtgata 2220 |
| aaacttctga | ctatgcgact | tctgtcgaaa | acgtctggtt | catactcttg ccaccaatct 2280 |
| tctttgataa | ggccgtggcc | ttgtgcagat | gggtcgccag | catactgtga attgtatgtg 2340 |
| tatgggttag | actctttcat | tgcctccaga | gattctaaac | tcttacgtga aggccataac 2400 |
| gcagacttct | cttccttcct | gttcaaatta | tacagaatgg | gaatggcatg agtgtagttc 2460 |
| tgcttcttga | ttaacttatc | ataccattca | gcacttccaa | ctcctttctc aataatcgct 2520 |
| gggatattga | gataatggta | tttgtcagaa | gagccaccac | ggagtatgta accaactaaa 2580 |
| tcctggtcat | gaactcgctg | catgatgata | accattggtg | tacgggcaca cttaatttgg 2640 |
| ttcccgtgcg | aatcagttat | gcaaccatcg | ttggcaagac | gggacataaa ggtgttatca 2700 |
| aatcggtcgt | tgatttctgc | tcgaactgtg | tcagagtagg | catctttcgg tttaataacg 2760 |
| tcatccacca | cgaaacaacc | agagtatttt | gcaacaagaa | gtccagcacc tttaccagtt 2820 |
| agcttaccac | cagtaggtac | tgcgtgcata | actccagctt | tggttgtacc ccagcgttca 2880 |
| agagaacgtt | tgttagggtc | gattctcacc | ttcggaaata | tgcgttggaa cagtgggtcc 2940 |
| atcattacgg | cacgaatgta | accactcgat | tcaagaacaa | cgtcttctgc atacgaggtg 3000 |
| ataatgttgt | gacttgattc | attgtggcaa | aatgaataca | agggcaatgc aatactcata 3060 |
| agctgggtct | tagagtgtcg | tggagggatg | gttactatta | agcggtcaat ctcaccgtca 3120 |
| acaaccttct | gaccaacact | gaatattaca | tcgtgaaagt | cctgtgcttg gaatgggaat 3180 |
| cccatctgaa | tatggaactg | ccatttacca | aaggcttcga | aacttttcat caagattttg 3240 |
| cgaacacgtt | ctgcaacctt | ggcagggatt | acagttgggt | ccacgttatg tgggtcatgt 3300 |
| agaatcttgt | ctacgagttc | atcggtgtta | tcatgttccg | agtttggctc ctctaatgtg 3360 |
| gaacctgcaa | cacggtcagt | aacacctgct | tgaatacctt | tcttcaactc atctgcatag 3420 |
| gcagtcgagt | ctttcttgtc | gccagagcga | agacgctcaa | gttgtgctct gaaaacggaa 3480 |
| cgcagtacag | catcgttttc | aagaccctgg | ccttctaact | ctgcttgaat tgttcttca 3540 |
| tagctgtcaa | ctattgcagt | gttttctgaa | atatatcgac | ggagcaatgg caaagataga 3600 |
| atacagaatc | tttctcttga | gacttttaat | acgtcaccgt | agtgtttggc gagatacgag 3660 |
| gctactgtat | cattaaactc | cggtccgagg | tcatcagtct | ttgacattga ttcgttctct 3720 |
| ttgttttttaa | tcacaatcca | ctaatggttg | agtttgcacg | ggattgatgc gaatgatgct 3780 |
| gcctaaacca | gaatcggcct | ttaaatacag | gcggtttagt | ggcatgtatg aatcacagat 3840 |
| aggacattgc | tgcgttatga | aatcatcttc | tgcaatttca | taatggcagt taggacattg 3900 |
| tattgtgcgc | ataagcgact | ccgaataaga | taggaggcca | gatagcctcc ctaattacgc 3960 |
| gtgtcgctta | atatttaata | tcgctccagg | ccatatcttt | atagaaatct tcaagatatg 4020 |
| cttgggtaga | accaacaacc | accacaatct | taaatgcag | tatcagcggc ttaacagccg 4080 |
| acattaaatc | ttcgcgccca | cgcttgatac | gttcgacgtt | cttgattgtg ttttcaccat 4140 |

```
gagggagcat gaaaacaata acatccgcac ctgtttcgtt gcgaactgca agtgcacggg    4200
tgagataagt cccgccacca gtagaggtga cattagactt gaggtatgca aatttaactt    4260
tgcggttatt tactacaaca ggtgaggaca gtttcatttc agataggttc cagatttatt    4320
tgtaacgttc ggccccgtga gtgtgggcac caattgaagt tgttcctgaa acaaaggccg    4380
ttgtgccttc gccaacgaca gacatgctgt gcgagtggga gccgtcagga atatgtggtc    4440
tttcatgctg accaagttcc acacgaccag ttgagccaaa gccaccttca ccacgaccag    4500
ttgcattcaa gcggtcaact tcaacgaaat ggtgttgagt agctttacta acttgcacct    4560
gacaaatacg ttcacctggc tgaaccacaa aggctgtgtc cgagtcgttg tgcagcttaa    4620
ccataagatt gccacgataa tcggagtcca gaattcctgt gcagtttgcc aggcgaatgc    4680
cagacttaaa gccatgacca gaacggctat gtactttgag ttcgtatcca attggaatct    4740
cgaattggag gccagtatcg aaaacagcag agcagccggg attgataaca acagtgctat    4800
cggagatagt gcaaacgtca gcagcggcag cgccagcagt agcgtacaca ggtaatttcg    4860
cattaggatg cactcgttta actgcaacaa cttgggtcat acaagacatg attatttctc    4920
tacttgataa gttacgcgtt caatccagtt gaacactttg aatacagaat cacccacttt    4980
accatcaact agatgttcat ccactgttac gcgggtaggt gtgtctggga ggttgatgta    5040
tctgcgagaa tcgcccgtga aatcaaaacc atcgcgatgc aaacgaacaa tgagaacaaa    5100
atcgtaagca gactcaatgg caacgacttc atcaccaaaa ccgccatcgg gataaatgac    5160
attaataatg ccacccatac gccccgcgag ttcttcaaca cgagcagctt caaccttacc    5220
gaagtagtct tgtccgtggc gaggtttata cacatcttcg ctaacgtgaa taagagcctg    5280
acgaggtgtt ctgccaccaa gacctgcaag ggagatagag tctttgaggt cgcggtccga    5340
agcgtagtgg ataaacttgt ccacatcaac ttgaaagtgt ttggcagtat gctcatacag    5400
tgcatcctta aactggtgtt taatgaattt gcgtctgcca agaaagtaag gttcctcggc    5460
agcaacaatc ttatttgcaa tggtgtcttt accgcagcca ggaggtccat tgagaataac    5520
agctagtcgc ttaatcaaaa ctttcctcac ttttgtctgc acgtaaacga acgagtgacg    5580
ggaaccggaa cttaccagct tctgtcttct cacgatatcg aacttgcata atcgaaccaa    5640
ttagctcgtg gcgatgttcc cacaaccact tacgaatcaa tgtgttagat tctggaatac    5700
catggtctgc cagacaatct ttcaccattg aaccagcact gccgtagttc gaggagatag    5760
aaccacacat acctttaaga gcaccagtac cttctttcat accagtaatc ttcacatcgg    5820
catatttata tggtacaatc ttccaccatt taccttttgc atcacggaca ataatacctt    5880
catgaccaag cgccagatat ttatccatca atgccttaag gttttcattg cttgggtctt    5940
tgcaccagcc gatgtacaag cgtgggtcaa cagcaccatc actcaactca tacacattgt    6000
cttgggttag tgggatgctt ggcgggtcaa tacgtccgag gatgctagaa gtctcattcc    6060
aactattacg gaatatttca gcatctctga actgtaagtg gtccaaatga ggtaagggtt    6120
tggaattacg actccagaca ccacctgatt tattacggat agctcgaatt ccgtcaatct    6180
tgatgaagag ttcacagcgt cctttgattt gacattctgg gtcttcataa tcatgtgcgt    6240
gagcttttgt gtattttgta ccatcatcga ggagcttaat agacattaag attctttctc    6300
aggtattctc gaacagcatt cttgcgtccg attttggttt taggaactgg ctctatttta    6360
gcaagattgc acttggcaat ttgctcttcg tcagacaatt tggcaaatgc aatacacttc    6420
ttctcaatga ctgcatcacg ccgtgatacg ccatatcgtt ccatgtatgt aataatgccg    6480
```

```
tgacaatctt tacacagcaa ttccaaatct tctggctgaa ccagtagaag gttgtccaca   6540
aagcggtgca ggtcttccaa tttaaggagg ccaccaactt gaactttgtg gtttacttca   6600
atctctttga gcttatacaa cttcttgcaa tggtagcact gaatgtggaa gattggtttc   6660
tttgagtcac cgaccttcaa tgcaatgcgt cgagattgta ttagcgcgag tttgcttggg   6720
tgtttagacc aaacacttcg aatagcagat tggagccaag atacaaactt ggcttccgtt   6780
ccacaataac cgtaagccat tccaactcca attatttctg gaggtactct tcttgagtga   6840
ggatacgatt ctctttaagg tcaaagtatt cgttaatgtt cttgtaatgc cacaagcgaa   6900
cacagttacc cttttcaatt tgatggtgca tgtaaacaag acgggcccact ttgagcagct   6960 cttgttccca accatctccg aagcgcataa tgtatgcacc aataactttc ttcaaacctt   7020
ctgcatagga ggttgtacca tccagcattt cgaatgaagc aactgcacca ataccatcac   7080
gacggaaata agtttctccg gctttggcac cagttttgta aattcttttct tcaagaactc   7140 cgcaacccat aacgttatcc gttgagtcgc caataagcaa ttgatgcaag aagaatttag   7200
ggccattgcc tttaacttct ttcttcttcg acttgccatt gtccttgatg attagcttga   7260
gttcgccgta atccttcgga gttacaacct tctcaccaat accctgggtt tctcgttccc   7320
attggtaatg tttaattact ggaccagcac caccattctg cccgatttgt cgcaagtctt   7380
tgtccaacga cgcaatccag acttcatcat atgtgcacgg accaatacga gtgaggctct   7440
taatctcatt acgtttaccc attgtcatgt catattcatg acgtgcgaat actgcgagaa   7500
ggtcatctgc ttccagacct ttcatccaat acccattcca tgcaacaagc aagtgggcct   7560
tggcgttctt taagttttca ggacgccaca catccttgcg atttcctttg tattcttctt   7620
caaacacgtt gcgcattgtt ttggatggag atacaaaacc cataatatgc gttgcgccag   7680
aacgtttaga caagaactcc atcttggagt ccattgacat ttgaatctta gcaaaattaa   7740
tatcttctgg ctcttttccca aattcttctg cagcacaatg gctaaatgcc accatgtcaa   7800
aatctacgag caaaagaact ttcttcttac ttgccattta acgcttctcc gttatctcgg   7860
tgccattctg catgatgctt cctgcacaac caacgtacgt tcattggctt gagatagtca   7920
tcgtggtgag caatggccga cagattgcca caacactcac aaggttgttt agaaatcttc   7980
cctctacgca atgcatcatt taccatacgg tgtgcacgaa ttttgtttgg gaagttgctg   8040
cgatatgcag cagacgatga atacttggtt tctttgtttg cctccaagta agttcttggg   8100
ttctctttta ttctgttaga gtttagattg taatgttgtc tgctcctcgc attcttgcaa   8160
gatttgcaca tagtatcacg accatctttta ctcttcttgg tgcaaccaaa gtcagtaaga   8220
ggtttgggta cactacaaat acgacagcac ttcatttaaa ctccaaaatt aaaggctccc   8280
gaaggagcca tattgttcaa caatcagaag ggcattcccg taccgccagc agcaccacct   8340
tcagcttcac gctgtgcttt cgcagcagcc tgtgcttcca gttcagcttt catagctgca   8400
tcaacttctt catcagaagc ctgattcggt acagcgcctt catcggcagg tttaccgcct   8460
aacagtgcag acagcttagt cttgtagaaa tcaacaccgg aagtaatacg gttcttgatt   8520
gcatacggag attcgccacc tggcagtttg ttgaatactt ccaagtccgg ctcagacatg   8580
tcaaagaaga cagtcgggtt aaccagagct ttagcttctt tcttctcttt agatttcatc   8640
ggagagaagg tagcaacttt gtttgcaacc tggccagcat tcttacctga ctgcttggta   8700
tactgaacaa tgccaacaat cagaggttcg cccaaccaat ccggcaggtt cttggcagga   8760
tggccctgaa taccttgttc cagattaggt ttaacttcca gtgcatcaat cgccttagcg   8820
aatttgtaga tgtgggagtt ctcacccatg aagccgtcag cattataggt aaactcaaag   8880
```

```
tcaaaccaac gtggcttgtc ctcaagattc ttcgccatca tgatgccgtc atcttcgtct    8940
gggtcttgaa ccatgaccat tttaccttca ctgtcaactt ctttcatgta ctcgtcgagc    9000
agttcgaaag tcaccagaag tttcagggac ggagtaggat atttagcaga accaggctgt    9060
aagcccaggt cgataatacg gcaaacacga gcaggataac cacccgcttc cagtaatggt    9120
gcagcagaag gagtcttgtt cgaggccagt gtaggagcag caaatgccat tttgagtacc    9180
tttaaatttc agtttagaag ttagtcgact tgcaacgtag caagccggaa gtcatatcca    9240
actaatgctt cggacagctc ttcaattgaa gacgttgccg aaattaaagt ttggatgttt    9300
ttgaatgtct catcattgaa tgcttgagac tgtgggtcag acgaagcgaa tacttcgtcc    9360
ttaatctttt caagaaacgc cattacggcg tcctttgctg gaacttcgga atcagcagca    9420
aacatatggt gctctaattc ctgcatatca aaaatagaat atacagtttg cattagtgaa    9480
tctccgcata gttatcaccg aactgcacat cacatgcaca atcacggtta agtttaagtt    9540
ctttgttggt tcggtccatt gcctcattaa gcaagtccgt ccacaaatca cggaaacctt    9600
tcttaacttg gagaatcaat tcatcatgga attgcccgga cagaagtggg tcacagcccc    9660
aacgttcatt acaaattgca atgatattgt tacaccagat atcaaacaca tatgcaccag    9720
taccctgaca caatgtggag aagcggtctt tctctgtacg cagggaatac cagaatttgt    9780
ttactggatt ctgttgccac atctgaccat caattgttac cactttagtg tttgcagcaa    9840
tctctttaat agaccagttc aagtcccaat atgctttatg cagtcgtgca gcagtagtct    9900
ggtcacagcc agcagaacga gctacagttg gtacaccagc accatactga caagcatagt    9960
ttgtggtctt aaacattgga cgttgtttac acttcttaat tccgtcctta tggtcctgag   10020
attcttgttc ggtaataaat ccaccaatta cgccgattgc aaggtgggca tcatagtctg   10080
gtgccaactg cttcttaacg tattcagggt catacatcca ctggaagtgg tgcttacagc   10140
ggtcttccaa agaacacaag tcagagccta actgttcata gtcttcgcgc cacgcttcca   10200
gcattgaacg cagttcttca ccgccaaata cacgaataga agggaggtta acaagttcgc   10260
gatgtttaag gcgtaaagta ttggtaaggc caccacatcg tgcagtaagg aacccatctt   10320
catcgacgtc gcgaaggaag ccattaacaa cagacagacg tgtttatac acgcccatcc   10380 caataagatg ttgaatacca gagtcggggt ttctttccgc cagcttatgc aagctcggac   10440
atatttcagg attgccatct tcatccttca cagtgatttg cggaatctgg cgagtttcac   10500
ctgtttcctt gttacggtca aacttaaagg tttccggttc ccaacccagg ctgaacaacc   10560
aatccttaat ttgaacatgt gaaccagcat taggcttctt ataaccttta agaactttga   10620
tagccaggtc tgggtctttc cagtccaaac cgtttgcatc acaaatagcc ttccacttaa   10680
ttccagtggc agacagttgc ccgttcattt tgtggcattt agctggacgg gttttgataa   10740
catattccgg aacacgcggc attgatgctt ccaatgcgtc cgtcttctct ttaatcattg   10800
gctccagctt ggccttaaac gccaatgcct tctcaatgtt tagcttccag cgagtacgtt   10860
gctgaataac ttgctgacga cttttgtca tcaggtattc aacgaagcgc ttaacttcgc   10920
taggagattt ataaatcttc aagagttgaa tgtattgctg ttcccacagc ttcaactgaa   10980
tcttgcagtc ttccatcaca cgatggttgt actcttcttg agtttgattt tcccaatctt   11040
caatgactgg ttttggcaca ccaaactctt cgccgtaacc ttctaagccg tgcttaacac   11100
gacgaggttg cagataccaa ctgataaaca aagtatcaat taaggtacat tttgaaacgt   11160
cgtaaccaag gaacctcagt gcttcaaagt caaaggttgc gccgttgtgc atgattagcg   11220
```

```
ttgggcctgt atccagaaat gcctggatag attttctgtc ggtccactct attacagttt    11280
cttcacgagt tagaacatca atatatccaa tgttgtgaag acgtggtgca gcttgcttac    11340
gcatttgctc caacaggcca gttgtttcaa tgtcactggc gtacatgttc tcccaaggat    11400
acaacacagt atggctccaa tggattggtg agggctacgc tggtgggcga accatgcagc    11460
gtagcagctc tgttattgat gaggaccgtt cttcttagta agttgaacaa tctctttagt    11520
ttcgaacagc gagtcatccc aagaacgttg gatgattcga ccggattcgg tgtcgtagta    11580
cgtcttgaag ccttctgttt taccactctt acgagcctta atggaacgaa tgatagaaca    11640
gtttgggtca actgcctggc tattacgctc aaagccgaac ataccatgag aatatttagc    11700
agcagcacgg gagccagtaa agtctgactt cttaatacgt ccaccatcct catgaggtcg    11760 ttgaccttt gccacagggt taaggtgcga caaaatattt acatggaact ggtattggtc    11820
tgccagctta gtgatatctg catacagctt acctaggaag tcgttcttct ctgaggcaga    11880
aatcccttcc gataagtagg ttaagttatc aaggacaaac atatcaatgt ctggcccaat    11940
ctgacgaaga atcgtcttta acccatccca ggtttcataa gggtcttctc cagcttgctt    12000
gcggtcccaa atctccatgt tacgaagcat cttcgcagca gtttgacgga acttggtttc    12060
atcatatcga gggtcttcac gagtaaacgc gggttcccaa tatggcaagt tgtcattgag    12120
gccagccatt cggcgcaatg tttctgtagg agtttcctcc atgtatgcag taaacactcc    12180
ccaatcatgc ttggtaatgt tgtgatgcac aatctgacgg gacagcgtag ttttaccacc    12240
accttctgca ccaccgattg taataacttc ggctcgacgt tgaccaaaca ttaggtcggt    12300
caacttgggc caaggatagt ccacaccttg ttcaacctca tcatcaagtt cttccataag    12360
aagttcttta ttgacaagtg ctgtaggaag aggacgagca gcacggaaca caacagcaga    12420
ttgagtagct ttgagcaagc cacgcttcaa acaatcgttg gcatcgttag ctggaagtgt    12480
tgcaatcatt gcaccaggca acaatcgaca cgcttctttt gcagctttac gtccaggttc    12540
gtcatcatca aatacgataa caacctgttc ccaacgttgc ttaatttctt ctgcaactgg    12600
tgacaaacat ttgtgtacgg aatcacttcc atcactcaaa ctaattacag caaaatccaa    12660
atcttcatat gcaccaccac ggttcatggt tttgaggatt tgacgcaatg cgatacagtc    12720
ttcttcacct tctgtgatga acagtgtctt accgccaatt gcttttgcag ccatccagtt    12780
gtaggggtcg ttaccctggg tgtcgccaac cgaccacata actttcttgt tcagaagttt    12840
aatcttccaa cgaacaagtt taccattttt ggtgtagcca tgtgccagag catttggagt    12900
ctttccatca tactctgaat acagaagtcg aacaccagca gccttccaga actccggctc    12960
aatgctgcga tgggtcaagt caaacggagg acaagcagtg atttcatcaa cttcttcctg    13020
aatttcttct ggagttttga ctttaatctc tggaatgttc tccggattat tgccataagg    13080
atttggtact agaacgccac acgcaaagca gtaaccagag aagttcttat taccagcttc    13140
atcgacattc aaccaaacct gtaaagactt gccagatgtg gatttacagt ctggtacatc    13200
gtgcttaatc ttagccacac attgcttgac gttcatttat ttattcctgg ttggtcagag    13260
ccttccaaca aattgggaat agttctgaca tgatttattt cacttcttcc gcaaacaagc    13320
gaacttcgta ttgcgcatgt tcggaggaac gttgattata catagatgcc cagccataaa    13380
gtgagccagt ccaaatccat tcagtcatca tggattgtgg aagaaccatg cgagcttgct    13440
ctggggcaat ccccaaacca attaacattt catattctgc gatgcaagcc atgttgtggc    13500
cttccatgcg atacttaatg tcatcagcaa atcttgtgg caatggttgt gcagattgag    13560
tcatcaactt ttcaggacga ccaaacacag tatctggaat gaagaattcg acttcgattg    13620
```

```
cttcaccatc cttgtaacga cggctaacct cattccaact aaatccagtt tgatgtttgc   13680
caagctgacg tgcaatgaag attggagcct tgcaacgcag tgttacttgt gcgtgacgaa   13740
atggtgtaat gtgcttgtgc tttgcaagaa actcaatcag cttctcgtct cgcaaggaca   13800
tttcatgcga ctctgcaccg taagaaactc gcgcagcgtt aacagttgta aggtcgctgc   13860
ccatgtggtc aacgagtgtt gcagtaatca tttgctctcc ggttcatatg gtgggagatt   13920
aattagctcc gcaccatgat aatggtatta ttttaatgac gcctgtaatg acgcatttag   13980
tacagaacgc ttttcatatt cgcgttgatt gtacgtgctt gtcagtgctt ccgcagcttc   14040
tattgacaag attgcaaaac caccaaaggc attgcgaact tcttcaatat ccatgtgcag   14100
gacttcactg gtaatttggc tggctattac ggccttataa atctcttcag caatttcagc   14160
agttttcatg tttctctcca ggttaaattt aagtaagtgt cctgacgtgg actattacga   14220
acattacaat aaattggctt aaatgatgtt tccactgcgg ccaagacact tattaaattt   14280
gattcgaacc gcccaagtga atcagccttg tttatgggga ccatcgggga aaagtataaa   14340
cccgcttaat gctcgcatca tgtttgaaca ttaagaaccc tcgacttgca tatttcatgt   14400
gaataggaac atagtctgga ttttgaatcc aactaacttc gggatgagga gtaacccaaa   14460
cgaaagcctg aactttcttt ctgcacaaca caatcagcgc aactaagccg tatcgctacg   14520
gtatgccaga cgctaacttg agccttttgg acagaggcat aactgtttgg aaagtggtgg   14580
attcggcgaa ctccgcgttc acaattacac agtcggcctc ggatgcttca tccctatccc   14640
atcgtgcagg tttcattaac tctacgaatc cattgaattt ggcgaccgat acgttggtca   14700
gacgctgtga tgcttaacag aatcgccacc tggttcagac aacttcttac gaagaaattt   14760
ttcttctgca ttatatagaa atgcgtaata aagttgcttg gccttatgac gactacaacc   14820
cagagctacc tggatttcct gaaactggta tgtacgcact tcattgtgaa ttattgcgtt   14880
acgaatgatt gcacgaatgc taattttgtc catagaagac taccttatat agttgaggtt   14940
gcggccttta cgcggccaac gtgccattaa tgctggcaag acagagctaa cgttctcaag   15000
cacttttgtc taggtatgtt cccggccact gttctaggaa gtgactacct gaacttctcg   15060
cgttcactac ggggcttccg tcctcggagg cagcaatttt aattgttatg cccagagcaa   15120
tttgtaggct tgtttgagtt ggagtcctac ttccaaacgc atgggattac accaccaacg   15180
ctacaagtag ctagagtctc gttatttaaa gtcgcacact cgctcgactt tggctgtcgt   15240
caccttggtc agtcttttac accaccaact agctaggcca tgttcactca ctgtcgggta   15300
agtttagaac acttttgtgc ccacgtttca ttgtggacta aaatctgtgt tttggtttcg   15360
cgtgataaga ttttcacttc tgcaacatcc aaatagattg gttgtgcaat caagcaataa   15420
tcacttacga acccactttg agagcaactc actatcgaca ttgctatcag aactgctaga   15480
cacttctttc tgaacatgcg atttaatctc gacagattct tttaatgaat ctagttgctt   15540
ctctgtggct tcctgacgct cctcggcttt gcctgagctt ttgcctttga ggaatactgc   15600
aatgagaata ccaaatgcag tcaggacgcc aagaattatt gatttaagct gttgcataaa   15660
tcaccttaga tggcgcaagc accgcttgag cagtcgttat cgccctcacc aggaacgatt   15720
gcttcttcgt cctgcttctt cttaagttct tcaattgctt cttcggcagc accgaagtct   15780
aagttatcaa gtgcatcaaa atccataagg actccagtat tgcgaattat taaagtgggt   15840
ggacgaggtt ggattcgaac caacgacaca tctgtcgaac agattgctct acctgactaa   15900
gctctggagc agaccttctg agctactcgt ccaaagaata agagggggttt tgataacgca   15960
```

```
ggttttcccg aactgcgagg cttgtagaat ccgtgagtcg cctactgtgt tttgacataa   16020
cgtgggattg atggtcccga ctcacttcat ctcaggtacg aggcactact ttgcgagtgc   16080
aagcaggtgt tgaacccaag taccaacagg caacctgatt taatctacct ttgtagatac   16140
catcggttat gagcagttta tttccatgct cagggcaact cactttaggg tgaattaggt   16200
tacgcagtgc agcttcgaag tcactgccac aggcttgaga ttcctgtgtg gagggaaatc   16260
cagaggagca cttccccaag gagttacgtt tcaaattggc atagcttctc acactaaacc   16320
aattgaagac attccagtgt gctcgtccgt cctctagaaa tatccaactg cataattaag   16380
tttgtactct gtcacatccc cacgcgcact ggaggactta agcctgcttt gcatcgcaga   16440
atacaaatta attattgctc cgatttatta atcacatctc gaagccacaa tgcgccaaat   16500
ttggttacgt gggattggaa gaccacggag aggacttaaa tttaattaag ccgcaactcg   16560
catttcagaa tcatttgcat ttattttaaa tgaataaaac agtcgcaata actccaggca   16620
gtttaggccc gtcgtaagac tcagaaaact acttcaatga acactcttgt ctgggccacg   16680
agcttgggca tcggcctacc tcccaactct aatcacaaga atgctcattg aagcccactc   16740
actctggaat gggttcaagg cagcaccgga aaacttccag tgcatgccag atcgatttag   16800
cttagtctct caagtttgcc atcggcaact tagaataccg gagcttcttc aacagcagct   16860
tcggcagctt cggcaacact tgcgtcagca actttagctt ctttcggagt atcgaactta   16920
gtacgctcaa cttccggctc accagcttca acccacggca ggtagaatgc caggaactgc   16980
tcgatggtgt tcttctgcat ggagcgagaa cggtcgatag cgccaacggt gttcaggtac   17040
gcttcggcag ctttctcaat tttagcaccg ttttccagtt tgaagtcatg tgcattacac   17100
tctgcttcgg tcaggaacag ggaaccatcg ttagcttcgt actgagttac ggttacaatc   17160
ttagccattt gtatataccct tatattgaat agttttgcac gccacggtga cgtgacttag   17220
ataaaattaa agagcctttc tctttccaca tccaactaat gtttcagaac tgctctgatt   17280
cgtcaaacga ctcaatatct attgaatcgt tctaatgttt tatttactaa atcctttgtc   17340
tcagcgacag tgagttcagt gatgattgat tcgtcataac cctcaatctg gattgctaca   17400
aaacgcccaa ctccagttac agtgagtcgg tttgttctgt cacgaacaac tacaccagct   17460
tcttgcgcga ctgctcgcaa caatttccag cgtaaagttc ggtttggcac agcaaagccc   17520
tttgccgaga acaactcttt catgagttct ccaagacaaa cagcttcaat gttttgtcct   17580
cttccaacta attcttgcaa caggcacagt gtcaacattt ctaaattgtt gaagtgtcca   17640
gcgcgctcca aattaaagaa ctctggagga acagttgaac gagatttaac agcttgctta   17700
tatgcacgtt cttcttcctg tgcagcaagc atcagcatct ctggcttaat atacttcata   17760
gcagagaagc cagcgcgtgt ggctttaatt atgcgacaag cctctttcat cttgtagcgt   17820
tgccactcac cgcgcttcga ttctggatta aaatggaccc acataatgat aacatcttcc   17880
ttggcaagat agacggcatc attatcattg agccattgct tacacgttga tagtgcaatc   17940
tctttgtcat catcatgata agacatttta gtggccttgt aggatacgtt tgttcgcagt   18000
ttctgcgtcg attcccaaat caactaatgt caccaagcac tgcgaaatcc gctcttgcgc   18060
agctttctcc agaatttggt attttttcgtt gtcaacgcct aacacattct ggcatgaat   18120 gagtgtagcc attagaccgt gccccaaagc aacagcttgc attgcctgga gttcaaagtt   18180
aattgtgatg ccagcgagtt cgtgctcttt ctgataatc tcaatcaact cttctttaga   18240
tttgtcttgt aagttcaaaa tggaactccg taaatcggtt ggtttgttgt ccaattgcga   18300
gttgcgattt gcatggactt gtttggtccg cagtagaaat acttcttaac ttcggcaagt   18360
```

```
gtgtaactgg cactgctctt aagcaactcc ttaaaggtgt gcttccagaa tccatctttc    18420
tccgacagac ttacgtggaa agaattagtg ccgttatagt accaacgccc accaacgaga    18480
acgaagtgga ttgtttcttc ctctccttcc ccacttgaag ggaacattag aacatttctt    18540
agcgtcaaaa ctttagcaga atgcttgcga atcataggaa ctctccaatt ttcgattcag    18600
tgtttgtgac ttctcttctc atcttttagc ccgtgaaaca ggccacagag tagcgcagga    18660
aggccgaaaa tcgggccact gcctaccgtt tgtgtcaatt ctggataact gcattggcga    18720
agggttactc ccgttagggt gcgatacgct aatcacatga gtgtcgtcgc cttgcggctc    18780
aggcgtgtca cagaggcttt gcaacccttc ccaatacatt cacccaaacc acccgctttg    18840
gcatagctgg tggcgcggtt ttgtgcggat tatgccactc taagtcctgt ttgtccgact    18900
tcctcagagc accagcagct tgtggcacaa acctattttc gaatgactaa cataagcatg    18960
aggcattacc ctctaattat tcagccctaa cagcttgctt atttagttcc aattcatccc    19020
aatacatcgc ctataacaag tgaatagctt tctgtggata agtattccgg ccctttggcc    19080
tatgttaaaa gataaatgta tatgatggaa acattccatc gaaaagagct ttgtagaacg    19140
aatcgaacgt tctcacacgt cttggtacca gacggactac ctagttacaa agctcttatc    19200
tgatgttgtt tcaattcaaa ctaatgtaat tttgtgctgt actctcttcc caagttgtcc    19260
agacttggtt gtttgaggct gcgcttattg cagtggactt cctctacaat tgctagtgga    19320
aaagagtaca gacagaatta cactaattca attccaatta atgtttcaga attattccaa    19380
tattccaaac aaaagaata ataagaataa attaaaataa atgaagaaag tgcttgacac    19440
ccatttggcg ataagtgtat aatgcctttc ttccctaagt ggtcagaatc aaatcccact    19500
aatgtttcag actaaagccg aaggccaatg cgagtacaaa acccgcttgg cacttcgaag    19560
aaacccgcct ggaactatag tgttttccag tctgagtcaa atagctcttt cggtcgtgtg    19620
tagatggtag aagaatcaat acttaagaaa gtatggtccc cgtacttctt cacttcttgg    19680
taagcaaacc catctaccca acttccgcag tgagttttaa tctttgtagg cccaagaata    19740
cgatagaaag tgtttcgagg ctggtggtga acaatcaatc cagcctcaag ttcagcaata    19800
tttaaatcac gcatttaaga ataatattcc ctcagagaaa atgtagtcac ttccataatc    19860
tctggtgatt gcatcccaat caatatatgg tgcaagtcgg tctggaatat ccagtgcctc    19920
actttgcttc aaatattctg taattgagtc gcaacgtgca ataaacatgt cgttcaaatc    19980
atccacagtg aaaatatcaa tctcaccact gcggaatgct gcaagaatta catccaaatc    20040
agtatcaaca agcagttcgt tgaatttgtc gtatctgcga atgctgaaca gtccattggc    20100
aaagcaaact tcggtaacat cctcttcatt tgattcaatt acgtcatatg caccggcttc    20160
tgggtattca atgccgtatt cttcatgcaa atactcccgc atgtcgaaat catagtgacg    20220
ccaagacagg ccatcaatcc acgcatctac aaattcagaa ttagtttcgc ctgtgtagaa    20280
acgaaccaat aaggtttcgt ctctacgcca ggacttaagt tgttctactg cttgagtaat    20340
ttggttttcc atcggattct ccattgatga agttatgttg gaagttcgaa gtgcggcata    20400
tcaatcagct tcttcttacc tggtgcaagt ggtggatacg gctgattttc atcaatacgg    20460
ctccagtttc caccccaacg aatggtaatt ccaagctctt ttgcagcttt gaacatgtga    20520
tgagctagaa cttaaatcg ttcgaggtca ttccagtcaa tcggatatgg tgcaaggtct    20580
aaggcgttgc ctgacatgtg tcggctaact gaaactttgg ttgcacctg ctttaaaagc    20640 tcttgttgac gctcataagt acgcaatcct tcaagaacag ttacatcaaa cggcattgtt    20700
```

```
tcacatgcac gcttgaaaac tgccaccaat gaaggattta cacccttgag tcggtcaagg   20760
gagcgttggc ccagcttaac gttagacatt tttcagttcc tggtccaggg tttcttgcag   20820
tgttacaagc aagctctcaa gtgtttctac acgcttttcc agttcagtaa gacgttcttc   20880
ctgaatctcg ataaattgtg cacgattcat gaaaaccag acattatctg taaatagttg    20940
gatttcttcg gacgttgagc cttgccctct cagttttgca acgcgttctg attgatttgc   21000
agactctcgt tttgctgcct taagttggtc agccagttct tcaactttca cggaatggat   21060
ttcctgttgg gttgatggtt aatttaaaag atacaagctc ccgattgatt tcggttgttc   21120
cttctactgt ggctgtagtc agaatagctg catctttacc tactcgctcc aagaatttaa   21180
ctactcggtc gcgaattact gaccagtgac gatattcgca actggattca agtaagtacg   21240
gtactccatc aatggtaaat tcggatgacg tcatttaact tccttacaat atgtggataa   21300
cagtggaaat ttggcatgaa agaagtcaat gtcacgataa atctgtagca ctaaacgttc   21360
ctcagcgtcg acaccaacta aagccagctt actgctctgt gtgttataga acactgttga   21420
cattgggtta ggatttccgt tatctggaat ctcaatccat gtaccttcgt gcaaagaaat   21480
tgttacaata agtggctggc tcattgtaat tgtttcaacg dacattttgt acccgccaca   21540
ctgaaagctg cgaacagatg cttctgattt gaatgcgaat actccgaaca aaattgtgag   21600
tgcaatatac aaagttttca cggcattaaa atctccgaat gattttagat acggtgtgca   21660
gcttgccttt gtaaataatt gcacatccgg ctgtaataaa ttgtatgtta agtgttgaaa   21720
ttggttcgtc aacaccttca agataaatat cccacatatt atttactctg ttggaatttt   21780
aaggattcag accaactgca aacataagtg aatttgttta cagaaggtag cattaaaact   21840
ttactacctt tgtcgtaaca tttactgcac caacatggat agcttgagcc accaccatga   21900
ccacaatcag gacaaactac accttgcatc tttgctccgg agaaacctcc agacatatgt   21960
atttccataa ttcctccaat aattaatcga ggccactcga agtggaatga cctctgttaa   22020
ttacagcttc ttgataagct ctgcggattt gcttgcggca gctttcattt catcgcgtgc   22080
ggccttaaca actgttgcct tgtccacgcg aattgatgca ttgccaattg ccatcttgcc   22140
atcttctgtt gggggaagct gggttaaatc aagcatttgc tccagctttt gcagaagaat   22200
acgttgtgct tcgattgcat tttgaatatt taatgtttcc attactgctt ttacctttct   22260
cgaataagtt ccagttagta tcaggcgcac ttgcaaacct tttacaccat cgtagtcaat   22320
attgacttta ttgtatggcg agtttggatg cttgtacgtg tttgtaacag ttgcccaatt   22380
acccttgtac cggataacat cgccaacttc aacatcagca cctttaacat cttcttcatc   22440
tgagaatggt ttcactgctc cctcgtaagg aaggaacact ggctttatct cagtgttgaa   22500
tgccattgtt ggggtttcca agctggtgg ctcgttaaca atatggacta cgcggttttg     22560
taaaaagtca aagtagccta tttcgtggat taagcgaacc tcactttccc ccaggtcttt   22620
aacttccttt atcttaaaga gcctgattcc ataagataaa gtgttgccgg gtcgaacttg   22680
acttgccaat actgcgcgtg ttgttgcgcc cggttttgca aaggagtctg tagtaggacg   22740
tttatccaag atttttgactg cctggtccca ctcaaaattg aaacatccac cagaatattg  22800
cagttgaact acacccattc tgaagacata cccaatcaga tactctttac cttcatgaat   22860
tacaacgtcg ccagttttga ctaagttggc aggtatttca ataacgttag ttgccatgat   22920
attcctcacg cattgctgaa caatgcctac aaacccaaaa ggttacataa tcgttttcat   22980
gtgaaatttc ccaattatgt agccctataa aacatagaat tttcataggg catctccaat   23040
tagaatggaa tgtcgtcgtc gaagtctttc ggctcgttcg gattgtaatt actctgctgt   23100
```

```
tgttgagcag gagcttgctg ttgctgtgca gcagaaggtt gctgacgttg ctgttgctgt    23160
tgtgcagcgg cttgaggttg agctttggct ttagctttct cttcacgctt acgcatcatt    23220
tcatcgacct gttcttgggt cataatggtc aatgcaagtg aggtaaattc attaccattt    23280
gcctgcttgt tccaaccaga tacccaatac cagattccgt caacgttaat acgtccacga    23340
acgtcaggat gttttgggtc tttcttgaag ccatttggac cgatgatgcc agtgtttaca    23400
tctgaatatt gtgccatgat taagattctc ttaagttaat tacagtttaa gtttcagcga    23460
cattgctaac cacggaatag ctttgtccct catatccaac taatgttaga ttaatcagga    23520
acactcagtg aatgctcctt gttaatttaa caggatttac aatatttggt aaactctctg    23580
cgcaatttgc ggatttgctt tttggtcggc tttactggaa ggcgtattac ccgacaattg    23640
tctaagtaag agtttccaaa agactctcta aaccacaacg tccaaccagc ctcaccaacg    23700
gtattatata aacgagtgga tataatcatt atttagctcc actaagtgct ttgtcaaagt    23760
accacatatc tttggtaatc cactcaccgc ttggtgattt aatgtagcat gaaccattga    23820
ttgtgtattt gaactctgtt tgctgcaatt ctgcaaaggt tttgcactca tatttatata    23880
caaaatatgt aggcagtcca atgacaacca gaacagacag caacattagt acgaaaggca    23940
ctacaatatc ttccataacc caattcatta catcacccttt gaaataggaa ttgggtcgat    24000
tgatgattca ggtttatacc aactgacttc accagaatct ttcacaagtt cccaattatc    24060
ggagaatgta cgataagata aattgcggtt atcatcatta acgacaaaac ccaaaggaga    24120
ttgaatatac gcaccgagtg taccgttgtt gcgaggaact ccgtcaccac gacctgcgac    24180
gattttgtac ttcttaccgt tggtaaagtt gtaatttgtt ttaccaacat aacgcaaaat    24240
tgaattcttg ttcattgctt tagtttctcc aaagctgcta aaactgaatc tccagaaccg    24300
ctaatcacaa gcgtttctgc tggaatactg gcggacacgt aagagaatgt ccacttcaca    24360
attgtctttt gggcaaaata agaatacttg tcagacaatt caatatcttg tcttacatcg    24420
tttaacaaga gctcctgccc atttacagac aatcgcttaa acatttcgat ataattccta    24480
cccacgctta atcttctccc atttggatag gccaccttca aggctaaaga ttcggttaca    24540
accagattca tccttaatga cgaattgagt tccggtcagc tgaattggct cacgtgcacc    24600
aaacaacact ttaggttttg acaaaactggt ggcaagaact gcataaactt tgcttgggca    24660
aatatcaaaa gcaaagtcac gagtataaac taagtcacca actttcaaat atgctggcaa    24720
caagcgacct gtggctgggt cacgttgtaa acgagtacgt tgtttcataa atgctccaag    24780
ttaattaata atattcagca accactctca ttacaaaagt ggttgaggaa attatttaat    24840
ctcttcccaa gtccagacac tacctttttag aggagtgttt tccccatcaa cccaatatgg    24900
atttccaagc acattcttac ggtcactgtc cttcgaaatt aagattcggc catgtttgag    24960
tttcccctca atcacgtcac caactttagg agagtaatct ccataggatg ttgattttac    25020
acatttaaat ttagccatta ttgaagtaca ccttgctcac aaatatctgc aaattctgct    25080
tcatggtcac gctgccatgt ccagaatgta ccattcattg ggacgacagc acctttacgg    25140
aatgctggag aaatgctttc agcagatttg gttactttaa attccaaagg cgaaatagct    25200
tcaccttcaa tgattaagcc aattggaacg tagtctttgg ttgaagcaac acatttaaat    25260
ttcatgatat aaaattccta ttacgcaata ttggattatt gcttctatgc cactctgcgt    25320
gatgcttatt gcaaagccag cgtacattca atacaaaatt atagtcgtcg tggtgtgctt    25380
gtacgtcggg atttccacaa acctcacaca gaccttttat caacttacca gacctgactg    25440
```

```
catttcctac agtattgtat atttcaacgt actcaggtct attttgtcga aagacttgca    25500
tattgtttct ggctgtttct ttccctaacc tactattcct atagcgaaca tcctttgctc    25560
tacctgcttc tgtacttcta gcaatcctct gtgcagcact tctgcaatct ttgcaagagg    25620
attgaagtcc gtcctttgct ttggcagact tattatactc agtgtaggac ttaacaatcc    25680
tacactttgg gcagagttta ttcatggtag aggactccca attgagattc taatctaaac    25740
tccctgaaga aatccattgt aacaaatcgt atctttcctt cgtcgtcgag cacgttacag    25800
gagatttcgg agtggaccat acggcccaac ttcaaagcaa cttctgacag gtttgcttca    25860
ccagtgccag aaatcacttc atagatttta tatggtgtaa agccgcttaa agagttatta    25920
cggcttggga caatcatcat gcctgttcta gtagccataa taactcctaa gtttgattat    25980
tcggttgact ctgctggtgg cttcatgtct tcaatttgtt gaagtgcgtc tgccaactgt    26040
tcttggagct tgttcttctg ctccattaat tcatcgtagg cgctttgttc tgccttacga    26100
agttcacgaa gagtgtcaac tgtttcataa gactgagaca actgcgcttc ggttaggttg    26160
atgtggtcca ttacaaaggc caacaaactt acatcaacac gcatatatgc aattacgtca    26220
gtatttgcag gaatggaatt cttagcgaca tttgcaatat tcgagaattc gagtaaagaa    26280
gccatttaat taccttagtt tagattatga agctgcccac aacgagcagc accaaaggga    26340
acattaaagc acagaatact aatttcttga taatagccat tatttcacca ggaagtagag    26400
agcaatcagg aatccaacac atgcaatgat tgttggcata taattatcaa ttttacgata    26460
ttgacgttcg actggcttct tgcctttaat ggcatccatc agttcttgat gattaatttg    26520
ctgcatgaat gtgttgaatt gctggtcgtt cattatttac tccttagctt tacattcttc    26580
ccaacaagca cacaatcttt aagccatcgt gtttttagat ttgctgggaa ccaggattta    26640
aattcttcgg agtataccct tgtgaaatga aactcaggtg tggtcagtat gagcatccca    26700
ccactagttc ttaatagcag attctcataa ttcacttaat actccaattg ccaaatacca    26760
gattaacgat tttggccact ttacgtgctg gcatacgagg atttgcagct cttgccaatt    26820
ttttagcctt acgctttgaa gcaccataca tagccatata tgtaaccgtt ttggtcatat    26880
atttgagctt cttcatttta aacgtggccc accttccata aagctggaca tgaaattgtt    26940
tgtgatgcct cgaataactt tatctgtgag aacatcttca taaaactgtt tgttagtgat    27000
ttcaatacca aactcttcct tgatacgaac caccaactca tttgtagaaa catcaatcca    27060
accaccgtag ttgacaacca aacgctcttg gatgaattcg actttctctt catatgaggc    27120
caactcgatt aagtcagcct tcaatttaaa ctgcgtcatt tagcctccag aatttggctc    27180
aatgaactga acacgatttc ctcatgttcg tcaggcgtac atgcgttgat gtattcaaag    27240
tcatacccaa caaacttctc cgcccactgt tgcaaacgaa gtaaagaatt gaagtacaat    27300
ctttgctcta caccatttaa cttaaagtag acgatgaagt ccataattaa cctcgtgctt    27360
taatgaaatt agggtgagta gccattgcta caattttgtt gtgcttgtca ttctgaattg    27420
caagccaaac atactcaggg tgtgcagcag gtttccaaac cagacgttct ggttctccat    27480
aaatcggcgt gtcagccaac attactgcct tagttttggt attgaccaaa gcatgagaaa    27540
caacaccatc acgttgatg tactgataca gtgcataatt catttctgct ctccaaattt    27600
ggagggttta ctccccccc ccaacgtatt agacttcaat tggctcttga actaaatcag    27660
aggccgagat tcttttaaac tcttcctcgg taaaagttct ctcattgtca tttaataaaa    27720
caccaatgtt agaatcacca acgaatacag catttacatt aacatcatct tccaaaactt    27780
tttgcagatg ttctccgcca cgcgtaaaga agattgcacc atcttccaaa tctttaaaac    27840
```

```
gagtcatttt attctcctaa gttaaagaaa aactccctac agaacgattg tggaggtctt    27900
gtcttacctc aatccaccft aaagttgtag ggagttatat agtattcctg tgtgtgccgc    27960
cgtcagtgac ttcctagtct ggtgggcgcg ttgcaatcca gcaatatacc acacgttttt    28020
cacaggctat atatgtgaca cacaaagtgt ctaaaaacta caatgattag cttggagaca    28080
taatctctct aaaatctgtc acagaattta cagagatttg gtcttattca catgcaacta    28140
atcgaaataa tgacgtgcca acctaataca atattacccc gccaaatgag ataattgcag    28200
cagattggca cgaacatttg tagcactgga gttctgtaga agcagccaac ttgtttgtat    28260
ttggcacaaa cagctgaata cctatgtaca gaaaaccgac catttaatta ataaactaaa    28320
tgatttaaat aaagggtttt atcccaatat tgtcacaata ttacatgcga tgataaagcc    28380
ttcgcttggc tggaagccag tattcatgcg ggttgcaaga atattgggtc actactgata    28440
cagctattac atgcgaaatt ggcacaaata ctgttacaaa attaacatgc cagattggta    28500
gacgattgta tcttcgaggt gattagtcct ctaacaattc tgccacattc caacatgcca    28560
atttgtagca atatttacat gccatactgc gacaatattg tcacaatatt tgttgctcaa    28620
aatcggggcg ggctacggga ttagtttcgc ggctttgctc cgactcttct cttctttcga    28680
attctgattg aaagaaagaa gcatgtccaa aagttccagt cttgtcaaag ttatctcccg    28740
gcttgtgggt gggcctttat aataggagat gaaacaatac tgtaactaat agacatgctg    28800
ggtttgaagt caaagtttcg gatagatatt cctactctaa gtcatggttg ctggaactat    28860
aggtggccta cctagggagt tcaatgattg ccacatcatt acaacactgt aactcaaagc    28920
tgacatgctg aatgtttcta gaatgattca acattacatg cggaagattt ctccgtattc    28980
ttttacttca tatccaacta atgtcgaata ttgaaacaat attacatgca gcaatattgc    29040
ttgaatattg ggaattaaag gatttaatta ataaagagta agaaagggc catcacctft    29100 cgatgacagc cctgtttctc ttattgacag aagtagtaag cgtgttcgct catcagaagc    29160
tcttcagtta cgatgttctc gtgatacatc tgaatgccac caagttgctt agacagattc    29220
tcgaattgat tgttggttac aaagatttca acgtatgctg cacgaatgac ttccatcatc    29280
ttaggagcat cagctaagca gcaacggaaa caatcatgga ttgaagtgaa accacgaaga    29340
ccagcttctt tagctttaac tgcaacagta cgagcaacaa gtgcatcaat gccttggatg    29400
tagttaacaa cgaaagtacg cttgaattct tctttagttg ggttggattc acgaatggtc    29460
caaggcttat tctcctgaat ctgaccaaag ataacacgag tttggctgtc aacacgaatg    29520
ctgaatgcct cacagatttc acgagatggg aagcaaggct tcattacaac ctgaccatca    29580
gtgtgacgat atgtgatgta ctctttgttg agttcaacac aacggttgta tgcagcttca    29640
gcagctttct caatgaacat gttaatctta gcacctaatg cgttatggat tgcttccaca    29700
cacagttcag caaatgcttc tgctttctca acaggaatct ggagagatgc tgtcatgtag    29760
gagataaagt cagaagaacc agttaatgca gctttaccac caccatattg gatagccatg    29820
tatggagttt tgataaactt acgaccagct ttcggattca agaattcatc cataatttca    29880
ggagatggtt tcattgaaga acggtctaat aacttcaaca gttcacgaag agataactgg    29940
tatgggtcag atgctttagt ctcagaatca accagacctg ttgcacgagc catttccata    30000
ttgccagcaa tgaatgccag atattgggta ccagaacatt tagcatctaa gccaaaacct    30060
acacgagaat cacactcacc tgtagtctca aacttgaacc aatccagagc cagacgaaca    30120
taagtgaatg gcttggaagg acgttcagct ttaggcatgt tcatcatgcg agcaagtgaa    30180
```

```
ccagctggat tctgagcaac ataggttaag cgtttagcag tgcaccactc accaccagaa    30240
atatcttcca gctcagccat gaacatattg tatgcaatgg tagtagaacc atcttcgtta    30300
aacttcttaa cgatgttctc aacattgtga gaatacaagc aacgagcaaa gtcagaggat    30360
tgtgggttag gaccagcaca tgctacatga tacagacgac cacggttatc agcaaagtag    30420
tcagaataca gagtgtcctg agtcatcatt gctacagcat tgttccaaac atggagttca    30480
gtctggattg cttctggcat ctgcaagcca ccataagtac gttgctcaat catggactga    30540
atgatgcgaa ccatttcagt ctccacatgg tactcagtat cttgcaagaa ttcgattgca    30600
gctttcagag ttttggatgg cttaactttg ccacctttaa cgaaaggctt gcgacgagat    30660
tcagtagtga cacgttcagt gaatggcact gaggtatctt tggttgtaac cagttcaacc    30720
catgtatcag tttgttggaa tgacttgtct tcgttcatgg tgatgaagcc aaagtgctta    30780
gccaaaccaa tgaggttgat agctgggtca acatagtgca ttgctttcaa atcgttgtta    30840
taacggttgg catcagcaat agaagcagaa gccagttcaa ccatcgagat ggcaggtaca    30900
acatcgtcac gagtgaaaga cgtcatcatc ttgaagatgg ctaacgcagc aatagcacaa    30960
gtctgaggct gcatatagtt ctgtttctct ttggcacggt ataccagagc agtgatagca    31020
ggaacaacga atttgatagt ttgagtagag atagtagtca tttgtaagtc tccaagattg    31080
tgtatgattt gaatgaaacg gattataata gcgtagccat tacacaattc acgtccaact    31140
aatatcacaa acctgtgcca ttgttacaac agcacgagga ctttgacctt gactcataag    31200
cgaagcgcct aacttgttat ttgaaagccg ataggctgta ggaaaaagtt ggggtaggga    31260 ccgtattta agtccgatag gacgttgggc ttcccctcct cgccgtccca aaaataaaaa    31320
ttataatatc accacaattc cagtctcgtt aatattgcaa caattcgagt ctcgttaatt    31380
gaaacaattc tagtctcatt aattctgtgg caatattgaa ataaaaaaaa aattatataa    31440
aaatttatca ttcatagtca gacaactgtt cgaacaaatt tcggctagat acagtcgacc    31500
gaccgtgaac gaatttatat ccaggtacag ttgaccgacc atgtaccatt tggttttgaa    31560
ctttacgcat tcctaatatt acccttaata ttgtagcaat attgggaata agtaatattt    31620
aacttactta ttttattcta gcttaaagag aaacgacgct aacgcatcga atctcttctc    31680
gcatattaac tgacaaacgt tacaactcaa atccacccag agcatcggta tcaacttcgg    31740
catcaatttg tccacgaga tacgaactaa tctctgtttc ttgtggagca acttgtacag    31800
catccgaatt caaccatgca ttaatccaag gaattgggtt agttgcacct tgaatggag    31860 catccaatcc aactgcttgc atacgaatat tcgtgatata ttctacatat ccgcacagaa    31920
tttgcttgtt taagcctatc atggagccat cttttgaacaa ataatcagcc caatctttct    31980
cttgttgggc cacattttcg aacatgagtt ggcattcttg acggcattcc ttagcaattt    32040
ctgccatttc tgggtcatca acaccacttg caagaaggtt cagcatgtgt tgagttccgg    32100
tcaaatgaag tgcttcatca cgagcaatta ggcgaataat cttggcattt ccttccatta    32160
acttgcgttc agcgaaggca aatgagcaag caaagctgac ataaaagcgg attgcttcca    32220
gtgcattaat ggacatgagg cataaatata gcttcttctt aagctcacga agagaaacct    32280
catcttcatg cagatgccac atggaagtta gatgttgaag ctcgtcataa tattgggaga    32340
tgccgattgc acgcatttta atgtgctcat tctccacaat ttcatcaaaa ataacacttg    32400
ggtctgtcac gatattacga ataatatgcg tgtaagaacg ggagtgaatt gtctccgaga    32460
atgcccaagt ttcaatccaa gttttccagtt caggaatgct cacaattggc agcaaaactg    32520
tagttggtcc acgtccctga atggaatcaa gcaggatttg gtatcgtaaa ttgctggtga    32580
```

```
agatgtgctt ctcgcattca ggcagaccag catagtcaat tcggtcctgg ctaacatcaa    32640
cctcttcagg tcgccaaaag aaagataact gcttctcgat taacttctcg aagatgctgt    32700
acttctgttg gtcatatcga gcaacgttaa cgttctgacc aaagaacatt ggctctagta    32760
gttggttatt cttggtttgt gaaaaggtag tgtaagccat tacagatttc ctagatactc    32820
atagaattta tggccaccat aacgtcccaa acctttaaca ttcttgaagt tgcacttctc    32880
cgatgctgta caaaagtggg ttgctttggt gacagagggt tgattaaata gtacaaaaga    32940
gattgcaaca ttaatggtgt ccagaacttg ttgttgttct gtggcataat taatctttgc    33000
tacatgcttc cattgagcat tcttcttctt tgcttctcgt gtccatgcaa attgattgcg    33060
ttgatagaca acatcacaaa cggtgttagc gaatggcttc ccgaacttag ttctattacg    33120
gacgacatta gctaccagaa tcttttccatg tttgtcttct ccgcgagctt cataccagat    33180
aactttagta tagcattcta gctctttgcg ttgtgaagaa gatagtttca gacttccatt    33240
taaataagaa tgacttgcaa aatctgtaat agcagaattc actgcccaa ccgaagctgg    33300 ggcgttgatg tgaactaaag ctgtcagaag tgcaagaact ttgaatgata gcattcgagt    33360
tccttatcat ttcatcgtgc cttcttgaac cacgtcaaag gattaagttg tttgattgcg    33420
ccagagaaac tttccctgac agttgtgata atgaggtttg caccgatgac accaatcacg    33480
atagccaaaa ctaactgcat ggttacatta gtggtgaaag tctcaaatgt gccagctacc    33540
tgaaatgcaa acaggcctat taagctgcat agcgtcgcat ccagcaacgc cttgcttaaa    33600
ccctcactct catatgcccc acggattaaa gccgtcagac cagcgagcaa gccgtgccat    33660
acgccatact ggtgcatgag gtccagaaac atctgaatgg ataatcgttc cattgttttc    33720
cttaagccac ccgttttccag aaggcatagt aatgaacggc gttggtcaca gtgaaggctg    33780
tgccgcttcc ggttgaggtt gtttcattgt tgcttggccc accagtggtt aacgccgtac    33840
cgcccgtgtt ggcagcactg gagccaccac tcgtacctgt gtagttaggc aagtctactg    33900
agtgtgtgtg agcaccagca gatgcggcag ttccgcttac actgtgtgtg tgagcaccag    33960
cagagttagt ggtcatcgta cccagaccag taccagtacc tgcaccaatg tagttacctg    34020
caccagtgta accagttccg gctgtgtgcg tgtgagcacc gttgcttgcg gcagtgccgg    34080
acacactgtg tgtatgtgca ccactagaac ttgacgtcac ggcaccgtgg tcgtggttga    34140
tggagtgggt gtgggccatc gtatgggtgt gtgctgcgac accgtgggtg tggttctgca    34200
ttccgtgagt gtgtccagga atgtttgcca cagcaagaga tgcggtatca gagccaccag    34260
tggaaccaat ttgaccagca gttgtaccag cttcagcaga agttgcagca cgagcagagc    34320
gaccatctag gatttgttcc caaactgtac ctgggaatga attatttggg ttaacggcat    34380
tgtcaaactg caatacaata ccaattgggt atatagtatt aaatatgttt gacgcatcta    34440
tctgaagctt ccacggaccc cagtccacag ttggggactc ccttgtgcga acatatagtc    34500
tggcaaagtt gtatgtagtg tacctttgaa tgcttagccc cgttgatgtc cagggcatta    34560
cctcaagcac accagcaacc ttttctggta tgtttattag tgtggtggct atattattgg    34620
cagcaaccat atatatgcca gacttttcta caccggagaa gtcattaaag tccagcccac    34680
tggttaggga ttcggcatac ctcgaccact tctccttaac caacgcatct aaagaataac    34740
ctttagccat tttgaatcct ataaagttga aatttgcttg gcagttagtg cagtattcca    34800
aattctgaat gcccttgctg caaacgttgc gcttgttact gccgccggaa gtgtccagaa    34860
tgagaataca ggtctgcggt cggttatgcc aaagctagtc gtattgtatg ttgccgccaa    34920
```

-continued

```
caccccatct ataaataatt gtatagatga tgagtctatt tttgcacaca ccctatacca    34980
ttttcccgtt gcagataaag cgttggcaac acggactacg ttagaagata caccagcttg    35040
gtccctgtat cttacaaata cagcaccact atattccatt attattttga acgactcaaa    35100
acccagaccg aactgccagt tgttgtccga gccagtctgg acaccttct gcaaatctac     35160 acatatcgta tactctccag agtctggcag tgcggattcg tttgtccaag ttctcgctgt    35220
acctgtatta ctggagtacc aagcaccacc aagcgaatcg ctgtacgttg gctcgtcagc    35280
ataggagtta aacacaccaa caccctgga tatgtttata gacctaacca actgcatctc     35340
atacgatggg tctagatggg catacccagg ctcttgtgct gccttaacat ctgggaagtt    35400
tagttccgtt acaatacgcg acttacttgc agcagtacct gcctctggat tccctgtggt    35460
tccgttgact ccaaggtagt agctcccatt acgaagatac agaccaccgt cgtttacaat    35520
ctgggcagtc ttggaatcat ttagatacac agttgtgaaa gtaacttcac cagtgtatgc    35580
gccaccagtt acgggaacag caccaacctg agttgcagta agctggtgcg ggttgttgta    35640
gtccgttacg tgcgcctgta ccattgcacg atagttggca acaatcgaat caagttcgga    35700
cttgttgtat gcaccaattt gtgcagcagt tactttgtgc gggtttgagg ttatgtctgc    35760
aatgtgtgca ttgattgctg ctacaattga gtcataattt gcacgagaaa cttggatgga    35820
gcttggactc cactgtgcag agtttgcact tgggcgtagt gttttgttag gctggtgac    35880 agtacaaaca tagatagtct tgtttgtttc gtcccaagcc aaactaccaa cgccataact    35940
tacatcattt ccccactcaa agattccacg ctctgcttgt gcaagcattg tggtgtcaat    36000
cttgtattgc aggtagttaa gaacctgata ggtcggaatc tctgcaaccc aacccttgag    36060 atattttca tcacctgggt cacgtcttgc gacagagttg tttgaagtcc agactcggtt    36120
cagtttagga cgaattgcca ttatggcctc actaacattg atttctgata agcggtaagt    36180
gttgggtaac aagtaatact gacaatgtat gcagcatctg atacacccaa gtttgtaagc    36240
agggtgttta ggctcgtgta tcctccagat ggagcatctg agttgcccct cccaagtgcg    36300
ccagcagagt ttctggtgag tgcaactatg gttgtcggaa tagagatatt aaatccggaa    36360
aacgtgacag tgttgtcatc tatcttcaac ccaccgctag ggtgaaacac tggcgttcct    36420
gtggttgtga ttgtccagtc acgaacagac gaaccatcat taatgcttct cgcaaagtcc    36480
atttgcaaat atggtgtagg gagtgcaaac ctgtttcccc agcgaatctg aaattctgag    36540
taattcagtt ctgtcatcac tggatattct gcaccaccaa ctatgctcca cagaacattg    36600
ccaagtgcat caatggatag aatcctatta cctgctcgca tctcaattct cccatttcct    36660
gggttcattt gaattgtgat gtttgttcca aacttcatac cacccaacag tgacacaggt    36720
ccggaaaact tgccaccaga tgttggaagc gttccaagct gttgtggtgt tcttggtgt     36780 acgcgaccag tttgtagctt atgatacact atggtccttg ggtctgtagg gcttccaaag    36840
gcatcatcta tcagttttt gctataagtt ttatctgtaa tggtatccac agtttcttta     36900
tgtggattgg ttgcagccaa gtgattatcg tagagggact tcaagttact tacgtcatta    36960
aggtagtcaa ccctcttaag gtccatcacc tcttcccaac ctgtgggtgt gtatacacga    37020
acaacaccat tgagggaaga tactgcacca acttgataag tcacacttga atcaaactca    37080
gcaatgccac tgaacagcag agatataatc ttcaaatcac taatttggga taagaagttc    37140
tgccattcat tgggaggctt ttcagcttcc cagcccagat tggcgtacct gttttcgata    37200
aaacttggcg cagtggtatc caagtccggg tctttaactt caccatcctg cgcccaggga    37260
aaattaaact taagacgttg agtcattatt tctccggagg ataatctttg gaaccataaa    37320
```

```
ccagagcaat gttacccttta gtatctctta gggtaatctt aactccaaca ggcttaaagt   37380
tcgggagcat gtaggccatg agaactttct cggccacaga caactcttca tgaataatgt   37440
agtccattgt ctgaaaccct tctacgattt ggagtttcag ttcccttcct acgaccaact   37500
caatatacat gataagctgt tcaatggtgc agttgccagt tatcttaatg attcgggcac   37560
gtatcgcatc cttcaactga ccatctgttc gaacaaagtc cccagagtct ttgtcgtaat   37620
ctgatttcag aataccacca atacctgggt cgttgtcatc accagcagga aatgcacctg   37680
ggttggcgta gaagccaaag tacccaagtg ccgcagcacc ttgtattaca cgagaagctc   37740
ccacaatata cgcaaggtcg tcaaccatga ctccgaacga atctgctaag tatctgtact   37800
taactgagtc agtcatggcc tgtttaactt ctgcaaactc ttctaagaag attgaaatat   37860
acttacgaag gtttggcgat agtgcatact gtgaaagcag catatctaag ccatgtttac   37920
cagccatatt ataccgtcac atcagtgtaa gttatgttag cagcaacccc gcgagcacgt   37980
ttgtcgatat ccaattctat cgttgctatg ccagttgggt ttggtgcaat accaataaac   38040
agcgaatcaa tttcaagata ctgtgttgca gccatgatag gagcaaacat gttggaccat   38100
accacactct gccctggttg cagggagttg agatattcaa tggttgcatc tgtaagctga   38160
cgaatagcat cgttcgaact tatgttggca tttgcacgac gacggaacgt acctttgaca   38220
taaatgtcgg tgtaagttgg tcggctgaaa tgaatatagt gtgggtagcc tttagagtct   38280
gctacagtaa ttgtgatatc accatatgtc ggaactccac cagttttggc attatagatt   38340
cgacgtgcaa tatcattact cgtaccgcca tcaactacaa caaatacagt gcccgaaggc   38400
tgattgccaa taggagagcc ggtatcatta tcacgaacac gaatgtaatc aatatcgagg   38460
tcagcgagtg aagcatagat ggcttcaact gtggctgtgc tactgactgc cgtagtcttt   38520
tctcgacgtg ctcggagttg tgggtctgat tcatagttaa taccagtctc gccaactgtt   38580
tcattaatta cagaattcca tccggcaaca ggagttacga tttggttgat ggttctcggt   38640
gcaatataat actcaccagg ctcttctgca ataacagtta cgtcacctgg gagtgttaca   38700
tctgtgtcga gaataaagcg catggtgcca tccgttacga tagaaccagc aggaacagta   38760
gttcccatat caccatcgca caagacagtt gcttgagaag gcttgtcaac atatcgaaca   38820
gtatttgtaa gttcgcaaac gttgtccagt ccaattcctg atacagcacc tggacggaat   38880
gcgttaaata cttgttcagc ctgttcccag cacgaggcga tttcatcggc cataattcca   38940
atatattgcc cgtcaggaga ttccggactt atatcaaagt tggaaccaaa tgcagcaatg   39000
aatttgttat taagacttga tacaacgtcg gccacaggct tgcgaacaaa accgttctct   39060
gttacgccgt atttgattgt tgccatgtta agaattccgt gatgttgcca taatcagaca   39120
atgcagtaaa ggagattcca aggcttcttg ctcggtagtc tgcatcaata tctatggata   39180
taagttgctg gacaccagca gttccacgga taatgttggc tattgctgcc tcaatatccg   39240
agggacgcac ttgctttgtg aagattgctt cgaaccacgg caagcccaac gaattgtcga   39300
gcttccattc tccgaagatt gtcagcaatc tgcacttaac caattgagcg acttgagcag   39360
cacctgaaat acgagttgtt ccacgcccaa taataatgtc gtggtttgaa tcaagagcta   39420
aatttccagc cattatttca tcggcccaac atcgccgcct tctgggttag tgtgagtgtg   39480
accatcaacc ttaataccat taagagtgag ggaaccagtt tgaaccatat taccatccat   39540
cttaaagtta ccagtgaatg ttgcagtgga accatctttg gtgccagata cagccatacc   39600
acctaacact gttaaggatt ttgtaacggt tgtgtcgcca tccagtgtaa tctgcggcgc   39660
```

```
tttaactgta gcttgcgacg taacttcaat gagaatctcc gaatcttttg tgatttgaat    39720
cttcgcagca cccgtaatga tttcaattaa accatcacca tgcaatgtta gtctttggct    39780
tctgtctgcg ttgcgcagtt ctgttactcc accattaaat cctggaataa ctttagtcaa    39840
aggctgggtc ccgatagtac atacggcagc attatgagag aacagttggc tgaactctgg    39900
ggcaggtcgc ccgtttacta ggccagcact actcttgttc tccgacaacc aatggtctat    39960
tcctcgctgg gagaaatgga cgtagcatgg agttccatct ggaaccggat gagttaagct    40020
ccaaccgcca ccctgaataa actgcacagg aacaccctgc aacctttgtt ttggctgcaa    40080
ggtgtaggct tcggcataac ccacaaacag gttttcgatt gcaagctgga cctcacaagt    40140
tgggttgct gcatcgaagt tgtaaatgtg ccctggataa cttgtgttaa tatcaggagc     40200
attttggtta ttgttatgac tagccacgtt cgagtacact ctcgtcaata atgaataggt    40260
agagttgtcg gtagcttgtt atttcttcac cagggaatac tgtgttagct gcatacatgt    40320
ttggaagcgg agtcttatat tgcttaagaa tatcaatacc gcatcgaata gggattccga    40380
atattttatt cgtggctccc cacgccaagt caaacatgta gcagtttaaa ggttcgttta    40440
agtacagtgc agacatttta actgtcacac cattaaactc gaacgataca tccttcctta    40500
tgctgtaagg cacactcttc acatatccgg ttggcagaag ttcggcaatt tgctttagag    40560
cttgatgttc ctgctcaatc ataggatacg ccccttgata gaagaaagtg gagaagccag    40620
cttactcaac ttacctttca gttggataaa ctgtttggtc ggaagagtgc caagagcacc    40680
aagtccagga agcggaacac ctccaagaac acccatcccc aaactttgag caacctttgc    40740
aaattcagag tagtcagaca ttgattccat cgccttgcga gcctcgctgg caagaacatc    40800
ttctcctatt gtttgcaact cttcaaacaa gatttcaaca gacaacattg cggaagtcat    40860
cttatcatgc ttggttttga ttgaggttac tacacaattc aaatagggtc ccagaatggt    40920
ggagatgtat aacttctgcc ccgtaacacg gaagctgtta aacaaatcat aagtagactg    40980
gattcggttg cttgtctcaa atgcagaggc aacgccacca gcaattccac caagaattgg    41040
gataaccgga ctattgaaga ttgcaccaga agcaacagac aaaccttgta cagatgcagt    41100
ccacatggag gagttctgca tgttgacagc aacagcggtt aacttaagta ccctgttctg    41160
attaataaca tggtcgctaa ccaggaaccc agaactaacg gggaacttgg ttacagttgt    41220
ttccgatgcg tgctcttcac tgaccatagc atcgaattta aaagagttaa aactttcgac    41280
ggcagattca ccaacaacag gcaagctctc aagagatttc gcaaacccac caaacagtcc    41340
tgactcttct tctttctgag atgcaggtcc attggaccac ataacaatag atggatgatg    41400
cccgtaactg aaattcttca agccagagga cacaccacca atgaggtcgg tatcaaagat    41460
agacattaaa atgactccat tgccattcca ctgttagcat acatttcctg ccacgcagct    41520
tccttaccac ccatcattgt attgccaccc aatattgcag tgattgatgt ttgataagtg    41580
gttgtgtgag tcgaaccttt atgcacaact tccatgataa agtatttgtc ttcaacagcc    41640
caccggaata cggactggtc tgtattgagt acaatacect ccectgaaac agaggtcaca    41700
ccattggcaa gtagcttgtc tccaagcaaa ggagatacat caagaatcat ccctggttgg    41760
aaagatgggt ttaggaatgt gtttaaagtg taggtcagaa ttccagcaac agggtttcca    41820
atgactgagt tggcatccag cttaactggc tctctatctt tggacattct gtttactgca    41880
tctttatcac caaggtgtc tgggaagatt tgcacttcac cagttgtaac agtgtatagc    41940
aagttatact cgccaagcat gttacgaaat tcgtttaaga atgtatcatg aaacacacgc    42000
ccacgaggca tcactgtttc aaggactgaa tcctcaacac caaatgtgga gatggtattg    42060
```

```
aatccatagt cagaacacat tgagcgcatt gcatcaatga gctttgttcc aggcttgatt   42120
gcagtcaact gtttgaaatc ggtagatgca ccatatgcct tggaaataca aaacaattgt   42180
gttacatgtt caggaggctt tctgtagcca actgcgtttg tgatgatgcc agagaagatg   42240
gttggcaaag tggtatttat ttctatgcgg ttgccttgtt cggccttctg accaaacttc   42300
ttgacaccac cactagaagc accacgttca tcttctgcat accctgcacg aatttcaata   42360
tacatatctc cataagtctt gtcctggagg aacttaactt cttctaatga caagttaaac   42420
agagttatgt ttgctgtatc ggcgggccac ccaacagtag aacggacttc aaaatcaata   42480
cgatgtgatt taaatactgt tcgaatgctt gggtcttctt tacgtgaaac tattacctca   42540
actctgcgta gccacggcat tgcaatatac ctattgaaat taatacatat tcaactaatg   42600
ttaaagtaag ctgggatttt ctccccaact cattaacgtc tttgttgcgc accgttgttc   42660
atgttcattt gttgagtcac agtctgacca ccaggaattg caactgtagc agaagcagtc   42720
tggttgttga ccttagcatc aatcttaaca ttaacaacag tttgggtttg accgtatgac   42780
attccattgc gggtaaaccc tgtagcacct tcttccagag attgagaaga cttggaccat   42840
tcacggaatg ctttgacgcg attctgtgct tgtgcaggaa cagcagtaag ccaatccaac   42900
ccattcttat caacagcctt gtcaacagtg ccaggaccat cggtgtaggc agccattgct   42960
ttctcgtggt cgccataacg cttatacatt gcgtcatagt attcgcgacc aactcgtgca   43020
tcatcttccg gagttccatc agacggcctg attccaaatc ctgggtcacg ggcagtcgaa   43080
gggagaatct gcattatccc acgagcacca gttggacttg ttacacgaga accatctttg   43140
ttatattcac gaccgccaga ttcttcctga gcaataaagt cgtaaacact tccagcaaac   43200
tctcgtgtcc tgttgaatcc agcgcgtaca ctgtcaagtg catcactgcc agcctcaaat   43260
acagaagcac cattagatag gacactttgt ggcacgttgt agctcggcag catccgtgcg   43320
cggcttccct gcaacatttc cgattgggcc ataccttcgg caaagtcgga gtttctaccc   43380
gcttctacca cagagccagc ttgctcatgg ctgtattccg tgcggtcgta ggcacgggcc   43440
atcccatcca gcccagccat ctgcgcagca ccagcgatac gggcctgact ccagccacgc   43500
tccttgcccc tttcctgcat gatgcgagcc agggccacag ggtcgccgcc tgtcgcacga   43560
atatcaccta tggtgagcaa tcccctactg ccgcgaacga tgttcacagc ggcgctgggg   43620
tcgccgttaa gcatggtgtt ataggcacta tgtgtggttt gattcagacg tgccgcttgt   43680
tgtgagttga gtcctaacat ctccaagcct tgcgacatag aggagtattc attaggattt   43740
atcacaccag catcaagcga gttgccaata aagtcattca tgtattcagc agcttcattg   43800
ccaatctgaa tagcaccaat gcctacagca gccatacgtc cagcaggagt tgccatcaat   43860
gcttgcataa ctccgttggt tgctgaacca atactaccac cagcaatgcc agcagctaac   43920
gaaccaccca tgcgaccgta gtcatcatag tagttgccac cacttgtgaa gttgccgcca   43980
cgaccaccgc caccgccaga gtatccaccg ccattggcag catcaaatct ttcacggttc   44040
cagcccattg aatcggcttt gccatcaaag tctgcatctg caccaatacc tttctgcctg   44100 tttcttcct gagcagcaag aataccttc ttaacagaca atgccatcga gtcatttccg   44160
gtgtcaccat ttccagtggt tgccggaaag ttttgctcgt gcattacaaa gtttggcttg   44220
tagtcagagt aggatgcttc tggattgtat gaagaacgtg aaccaataaa cgggtcttct   44280
ggagtaccag cagcagcaga atagccgcga gtagaccttt gacgaatatc tttccagatt   44340
ccatcaccag tcattgcact tcttgcacca gcaatcagct cttctcgttc taatccagca   44400
```

```
ttgtttctaa caaactctcg cccagcatca agacggccaa gcacagaatc aaggcgattt    44460
cggtttcttt cgtaccatcc ttcgtccttc tcaatccact gcgaacgtgt ttcgtcgttg    44520
atggtttgtg agaacaaagc acgagaacgg ccagaaacgt gcataccaaa ttgaatttgg    44580
tccatgtagt ctggatggtc gcctttaaga aggtcagcaa acttaccagc cctttgcgga    44640
ttcttgtgct cccaaatggc atcatcccca ataagaccat caggagaata catgaaggcg    44700
ggatagttgt catttgttat agcgccaatt tgtttgatat cgaatccaaa ttccttacca    44760
acacgagcgc gtgcttcttc ttccgtcctg tgaccatcag cgaacatctt tttggtgaaa    44820
tcgctgtgct ctttactacg agataagcca atcttatcaa tcatcccagc ccaaggtcgg    44880
gtgtatgggt tgtttcctaa gaaagttcca acagttgagc cagttatgtc ataattttta    44940
cggaagtcca gccactcttg gctgccctgt tctaagtcat ggaatcggac gggggactcg    45000
gaacgtcctg tgccatagtc tgaaacatca cggaatccag cactatccat atttgcaatc    45060
gcaagttcct cacgacgcat tcttgcagag ttccaattgg tggcctcccc aagttgtgct    45120
gtaaaatctg tagatgttga cagtgaatct ttatcgactc gctgtgaagc tcccttcatc    45180
tttggaatgc gaacaggctc ggcatccatt ttatcgtaag tgttttcgag gatagctcga    45240
acacttgatg cagaataagc tggctcatct gcaagttcag aacgaaggtt ttcgtatccg    45300
cttcgagctt cttccaaatc cgtgtagcgt gttgcactat ccataatcat gtcacggtca    45360
gatacttcgt gacgagtatt cagcatccct ttggagccaa ataaactttt ggcagcagat    45420
ttaacagctt cactaataga agaatacaaa gccttgcttg gttcgctcca acctgtgcca    45480
ccagttagtg acgcagtgag ggagtattct ggatttatgc cagaaccata agaaccaaga    45540
ggaagtccag atgcgttaag tggtgcacga ggatgtgcaa tgccagaaac aattgaagga    45600
gagccaattt gagggagtgc atccatgtaa gaaatatgtg gggccgattt atttcctaca    45660
ttagatgcgg atgtataccc aacttcctta aaggctgagg gtaactctcg ttccagacgt    45720
ttggcaactc gactaatgtc tcttgcgtat tgttcatgat gctgtattg ctcacggtca    45780 acatacatgt gagccatgta gttgtaggag tcagcaatgt ttccacggtt ggtggagtat    45840
tcagccataa tatccccagc ataatgacct gggatttccg gcataatatc ttgatgccct    45900
tgcaaagtat ctcgcatata ggcattaagc atgttgaagt taccttgcgg taagttcgga    45960
tttggctttg gcatgtgcat ccacacatca tctgtgctaa cgccaagcct ttccatgtat    46020
gcgtgaacag cttctacatg gtgtgatgga ccattcattg ctgcatgaaa tgcttctgtg    46080
tagccagcac ttgaaagcac ttgtgcaatg tgggcagcgt ctgaaatcat ggaagagtca    46140
cccaaagatt cagtaattaa actgtcatct tcgaacgacc cacccattaa ttctgcattt    46200
gtatccagcc atcccgaagc agcgctcgca ctaagttgtt gaaccatgtg cgacttcttc    46260
ataccagcat ggaaagtcag accgctttga gagcctaatg caattaactc attaacgctc    46320
aacttcatta aatctttttg attagccatt gtcttcatct actggttcga gtttcttacg    46380
caaatcgaga atgtcgtgga atagcaataa gtccataatc gaataggttc catcttgcaa    46440
ttcacgtaac ttgcagagag aactgtcttc gattatagga cgatgcagaa aatattttat    46500
gtcggggaac agggatacta aactgtctcc ggactcgaat tcttctgctc tgccagcttg    46560
gatgcttcct ccgcctccaa tcgtctctgt tcgttgattt cgagcccttg cttgaaaaaa    46620
tcaaggaagt ttgcttcgag cacgaaagca aagacatggc aagacaacat caattcgcca    46680
ttgaactgca tatcatataa tgcaggtttg atttcttgtc catctatgga cgagtgcatg    46740
ctgataacac gcttaaacaa ctctgtgaat acggtatgct ctacttgctg catcaagtat    46800
```

```
ataatatcag cgaagttata tttaccttcg atgaatggaa atactcgtga gcctaacttg    46860
cttaccaact ccgcgtgaag agacagtgca gccgaagccg acaattgtcg aacaacgact    46920
aacactgttt cgcctttgga gtttgtgaat tcacgttgaa gcaattcaca agccatactt    46980
actccaatta aacgccaatt tccggataag aaccagtctt aatctggagg cgctctacaa    47040
agatagacca cacgttagac gtgaaggaca caccacgctg aattgcaggt tgctgcaaga    47100
tagcgccgtt tacaccattg accagcacat cacccatctt gtcaacaatc tgaatctgga    47160
gcggttgcca cagagatttg ttgccagaca ggccagttgc ctgagttaac tgagcacggc    47220
tgtacaggat ttcgttccag tctgcggttt gcagaagcgg gaaagtaata gtaccggaca    47280
agtcagccgt agtagctaca gccaacttac catacgcgtc aataacaggc aggtgttgag    47340
gtgcgttacg acgagcagtg atgatggaat taccagaggt aaaaccatct acacgagcac    47400
cgtcgataat gaggtcggta ttatagaaag aatattgttt cacttatcgc accttactga    47460
acgaagttgc cagagataac tgcaccctgc aatgcgccag agccaattgc aatgaaggaa    47520
gtgccttccc agatacgagc acctttctga gattgcatca gagccaagtc ggtagccaag    47580
actttgtagc catctggata gaagttgcct tcattgtcgt aacctggagc aatcagacca    47640
ttggtcactg ccagttccag agccagggtt acttgctggt tcaccagagc aacaccagtg    47700
tccgtccaag gaatcttggt agtggaggtg tagaacaggt tgaacacgtt agcacgaatc    47760
ttggaggtta accagaaac accctgcacg gtatcgaacc aagtgccgtc agccatcttg    47820
ccgttgtaga acatagtgtt cccgccaacg ttgatgaatg cgttaccatt cacacgctca    47880
agtgcagcaa gctggttcgg ggacaggtca gcagtcttga tagctggacc ttgtttaaat    47940
gccagaacga gcgaagagtt tgcaacgttg aagttaacag tcgatgcacg gcccaggata    48000
gaaacttctg gatactcgtc gccattatca gacgcatcat acaccaacag agtgcgttgg    48060
aggttctgct ctttggcacg cttaaagcta gactcagcac caggaaccag aatctgcggg    48120
tcgctatcag cccaaccaaa tactttgcca tttgcttctg cccacttggc aacagtcatt    48180
tggttattac catcagcact gccacgatat ttgcggtcaa tagcaacaaa gaagaagtcg    48240
aacgtagagt tcaagattgc attcaagtca gtgccgatag atacttcatc agtaccttga    48300
acatgcacag ggcttgaagc agaatcaagt ttaaatgccg cagcagcaga accgtacacg    48360
ttaccaatga tggaatttac gccagtttcg ttggtagtga ttttgaaagt acctgtggtc    48420
tgcgtaacag ttgcaggaat gtcggcagca acaaatgcag cattaagcat tgatgcagca    48480
gcagcaaaat cgtctgcgga cgagaagttg attggtgcag tagacttatc aacgccgtta    48540
atattaatgg acagaacacc attagttaac gcagtaatgg tttccagagt cgcagcagaa    48600
gatgcggtta cagtaccagg agttgccaga gtaacatctt catgggtgat agcacctacg    48660
aggaaatact ttggagttgg tttctgagaa taccatgcca gagcagcttg ataaatttca    48720
ccagatggga aatcagcaga tacagcagcc atgctggtat actgacgaac aggaacagct    48780
tcgcctgggg ctggagtaaa ctccttgctc agaaacagaa gaggaccaaa accttccacg    48840
gcaacagcgt taggacttac cgcaatgttg acctggatga tgtcggaaat tggaattgcc    48900
atttagattc ccttaattag gatgggttca ccaccgtcgt agaatttgcc gccaacactg    48960
gcgtcagaca ttgttccaat gctcattacg tcttcacgta gaacattgaa tttgatttgg    49020
attccttctc ggaattccca attcgtctca agagttaacg aggcaagatt cagtggattt    49080
ttgtcaagtg ttgcaaagcc tttgctttta agcatggcct gaacatctgg acggaagaag    49140
```

```
gagttatcaa acttaacata ttcactccca cgacgtgaga agagaatata gaaggttaag   49200
attcgaatcc ctctcgtaac aaatacctcc tcaccatcgc gtacttcgat tcgagtctca   49260
tcaaagcctg gattaactga cgacacacat tttattgcgg catagttatc agatggtcga   49320
ggtgcgttta tctgcatctc ataagagaag cgtgggacgc caacacagac gtccacaata   49380
tccttcatcg cctgaatatc ttcatcataa atcatttctc tagctccttt gcagcaatga   49440
cttcaaagaa tccagctgcc ttgtagtcag aaacagaaat aactttataa cgaaggccgt   49500
agatagttag gacagacttc atcggcattt cagttcggga atgtacttgc atgaatgcag   49560
gttggcgctc tccgacttct gtagctttaa gcgattgacc gcttacgcca gaatccctgt   49620
caccataagg tatgggagta catcggatgg gtttctttgg agcatatgaa tcaccaaccc   49680
aattattttt gtcatcgtag taaccttctt gatatacctc aagatacata cgagtggttg   49740
tgtagcggtt aaatgctcga cgttggttaa tcaaaactgc gacccagggc taaccctcgg   49800
cccagcaaat gccattcgcc gccattgcaa gtaacgttga ccgtacacag tagacatgaa   49860
atcagcttca acataaggaa ttgttgaaat gattcggtcg ctaaactcta cctgaacatc   49920
gtccacatcg gtacgactaa caggcatagc tggcattgcg gcatcaccag gcattaggtc   49980
atcaattgtt gcagaccaat gcgctattag tgatgccata gctgggtcat aaaacccaca   50040
ccaacgcgat tcgattgtcc ccatgatgag ttttgcatct tcaactagaa tatcaaaacg   50100
ctctgaggtc atgtcagcca ttgccggata acgtttaacc aaatcggtca gtgttatcat   50160
ttacgccaac ttatcgtaga gtgccagttt aacgtcttcc ggcataccct aatatcaat   50220
accattctta gtcagaatag catcaatgtc aggcatacca actttcacac gttcaacaat   50280
ggtaagagaa ccagctttga ttgcttcttt aaccaggttg actttgcgag ttttgccagt   50340
actgtaatac tctttaatga caagagcttc tttaccggtc ttaacagaag caccgatatt   50400
ctcgtcatca agtggaacca cttcttcgcg cagttcttca acttccgtca gagatgccgt   50460
aagagatttg tagatttcat cgtcgatttc tacagttgcg ccaccaggaa tgtgaacaaa   50520
gtccagttca gatttgccag actttccctt cttatagaag aagaattgaa ggttgcgtga   50580
ttcgttgttc ttaatctgca ttactatttc tcttaagtta tgggcgagaa tagtcccgcc   50640
ctatttatca gatgccggag ttgatggaga ttgctgccgg atacatcgct tggaagccag   50700
cgaaacgacc acggcagga  acttcataaa ccagaccatg aagctgtact ggttgccagg   50760
tcagcggcag aggttcacgc agacggaaag tacggttgcc cattgcagtg cggcaaacaa   50820
cgacgaagca atcggaacca gcatcgccgt ggcctttgat tgcgttcaga cccttgattt   50880
tgtcacggga gttgatgaac tggttgttgt caatgaagaa ttgaccaatc gtcttatcag   50940
actgctcaga acgtgcagtg ttgaagatgt actgctcatg ctcaacaggc atccagattt   51000
catccgggcg catgattttc agagtagaag catacattgc agacacagca gcagtcaggt   51060
cagcaataac ttcggtcggg gtcttctcag cccacttggt ggaaccgcca gcaccctgag   51120
caacagttgc tttggtaatg tctgggtttt cgaagaagcc aacaaagccg ttagctttat   51180
cgccgtacca tgcagcagag ttaacatact gttcgtaacc acgaatagcg gcatttgctt   51240
tacgagtttc cagcgggagg ccagtaacag cagcggatgc cacttcatca atatcgtagt   51300
cgaatgcagt accaacagat ttaacaggga tactgtattc tttgccagaa atgctggatt   51360
taggcaggtc ggttgcacgg gcgttaatta cctgtgcttt accaacatgg ttgtaagaac   51420
ggtaggtcag agtgtttacg ccagcaccgc cagtggtgtc cacaccgaaa gcagcacgag   51480
cttccagttc tggatacagg gtgtcataag tttgagcttc aatgaactca agctggcgtt   51540
```

```
gaaagaatac tgcatcgtcg tcattcagga caacagtgcc agaatcctga atacgggtga   51600
tagcgtcgtt cagttcgaat tcagaaccgt ccgccagttt aatcatcttt ggcatgtaat   51660
ttaatccata ttgtttggtt aggcgcaact attaattgcg ccagtgcaac ttaagccttc   51720
ggcgtaatgg taatttcttt ggttgcagtt acgccagatg ctgttttatt tgttgccttg   51780
attgtcgcag aagtatctgt ggttgtctca ttaaggacag tcacagtgcc gtttgccgcc   51840
acggaaacac cagtcacggg aggtgtaaca gcgaagttat agtctgttgc tgtggagttt   51900
tcaaacttaa acagcttatc cacagtcaca gtagcatcgg atacagatgc gtcagcagtt   51960
acaactcctg ctacagcaga tactgtaggg gccggaggtg gcgttacggc tttgggacta   52020
cgttaatcat gaccgggaca acatcgccag cggaagccgg ataacgcagg gcagtcaggt   52080
tggttgcttt agtataccca gcaccaacac cgccaaattc accttcagtg gatacgccga   52140
tgttcttgtc ggtgattgca gttttcagtt taaccatgat tgggccagac agcataacgc   52200
ccagaggcca gccaacttta atagcaacag taccgtcacc aggacgagtg gcagattcga   52260
tgttaatctg gcgcatggtg atgcccagaa cagtgccgtc tgcttcaatg ccaggtttaa   52320
cctgattaga ggccgtgccc tgaacaacag ccagaccaaa gtttgccatt tcttcttcgg   52380
caacgtaagt caggcgctga gagttggtgg tagccaggcc atattgttca cctgcatatg   52440
cttcaccagt attaatagac caatcttgct ttggcattgt cttaccttat aaagagttga   52500
agcgttctaa acgacgtttg ttagcttctt cggaaataga aactttaggt ttacgagctt   52560
ctgaatcttt cttagcagag aattgcatag actgattcag ggcatctccc aaagtaatgg   52620
aatcgcaatc ttcaagagcc gcatcgaaac gggcggagat atagtcttcg ctcttatcgc   52680
tgaaatcctt gtcatgcaat ttattaacta cagccaactt aatttctgca tcggtcttgc   52740
cggagaaatc gaggttggag aactcgtcgc caagacgtgc cacatcaaca agcaatgctg   52800
tacgagcaat tacacgtttg tctacctcag cctgaatggc ttcatcggat agtcgtgcag   52860
tttctgcatc agcaagtttc tgctcaagga cactaatctt gtcaagcgct gcatcacgct   52920
ctgcttcaac aacgtcaaag gttgccttat caacaatggc aatctcttca ccagagtcac   52980
caatgcgagt agtctgagca cgaccacgaa caacaattgc agcatggtta gggataatgc   53040
gaactttatc gaagtcagct tcatcatctt ctgatacagc cagttcagca ttatggccca   53100
aagagatttg gtcaacgcca gaatcaacta atcgaatagc ttgctcgtca ttcaaaacga   53160
ttgatgcagc caagaaagaa ccgtctgcaa ctggacgccc ttcgataaac cctttctgga   53220
gttctttgtt gttcttgatg ttaacatcat ttttcggatg gccgatagtt accggaattg   53280
aacgacagcc ttcgatggtt gcttcgtcga ataatacttc cggcttggta cgaacacggc   53340
aaatagattc tgggtccaga tgt                                          53363
```

ENTEROPATHOGENIC *E. COLI* BACTERIOPHAGE ESC-CHP-2 AND USE THEREOF FOR INHIBITING PROLIFERATION OF ENTEROPATHOGENIC *E. COLI*

CROSS-REFERENCE TO RELATED APPLICATIONS

The present application is a U.S. National Phase Application of International Application No. PCT/KR2015/014330, filed Dec. 28, 2015, which claims priority to Korean Application No. 10-2014-0192982, filed Dec. 30, 2014, each of which are hereby incorporated by reference in their entirety.

REFERENCE TO SEQUENCE LISTING

The Sequence Listing submitted Jun. 21, 2017, as a text file named "08162_0031U1_Sequence Listing.txt," created on May 24, 2017, and having a size of 68,142 bytes is hereby incorporated by reference pursuant to 37 C.F.R. § 1.52(e)(5).

BACKGROUND OF THE INVENTION

1. Field of the Invention

The present invention relates to a bacteriophage isolated from the nature that infects and kills enteropathogenic *E. coli*, and a method for preventing and treating the infections of enteropathogenic *E. coli* using a composition comprising the bacteriophage as an active ingredient. More particularly, the present invention relates to a Myoviridae bacteriophage Esc-CHP-2 that is isolated from the nature and can kill specifically enteropathogenic *E. coli* strains, which has a genome represented by the nucleotide sequence of SEQ. ID. NO: 1 (Accession NO: KCTC 12661BP), and a method for preventing the infections of enteropathogenic *E. coli* and thereafter treating them using the composition comprising said bacteriophage as an active ingredient.

2. Description of the Related Art

*Escherichia coli* (*E. coli*) is a Gram-negative *bacillus* and has somatic antigen (O), flagella antigen (H) and capsular antigen (K) comprising lipopolysaccharides in its cell wall. The combination of these antigens contributes to various serotypes. In general, *E. coli* is divided to non-pathogenic *E. coli*, residential flora in bowels and pathogenic *E. coli* acquiring specific factors (anchoring factor, heat-stable toxin and the like) causing diseases.

When being infected, the enteropathogenic *E. coli* (EPEC) produces Shigatoxin or verotoxin, a similar kind in human and livestock so as to provoke diseases. A variety of serotypes (018, 020, 028, 044, 055 and 086 etc.) have been reported. The infections of enteropathogenic *E. coli* often occur in one year or less-old infants, because of contaminated milk or baby food, which manifests vomiting, abdominal pain, diarrhea, pyrexia and the like. They are also generated frequently in regions under bad sanitation.

Even if *E. coli* diarrhea is mostly caused by enterotoxigenic *E. coli* (ETEC), enteropathogenic *E. coli* is also another important pathogenic bacterium in pigs. The enteropathogenic *E. coli* reduces the growth rate of infected pigs, leading to death and leaves a lot of economical losses because it costs high to treat and prevent. Considering a significant damage in livestock industry by such *E. coli*, it is urgently requested to develop a method for preventing or treating the infections of enteropathogenic *E. coli*. A variety of antibiotics have been used to prevent or treat such enteropathogenic *E. coli* infections. However, according to the recent rise of antibiotic-resistant bacteria, an efficient alternative is urgently requested.

Recently, the use of bacteriophages has drawn our attention as a new way of treating bacterial infections. Particularly, the reason of our high interest in bacteriophages is because bacteriophage-based treatment is a nature-friendly method. Bacteriophages are an extremely small microorganism that infects bacteria, which are called phage in short. Once bacteriophage infects bacteria, the bacteriophage is proliferated in the inside of the bacterial cell. After full proliferation, the progenies destroy the bacterial cell wall to escape from the host, suggesting that the bacteriophage has bacteria killing ability. The bacteriophage infection is characterized by high specificity, so that a certain bacteriophage infects only a specific bacterium. That is, the bacterium that can be infected by certain bacteriophage is limited, suggesting that bacteriophage can kill only a specific bacterium and cannot harm other bacteria.

Bacteriophage was first found out by an English bacteriologist Twort in 1915 when he noticed that *Micrococcus* colonies melted and became transparent by something unknown. In 1917, a French bacteriologist d'Herelle found out that *Shigella disentriae* in the filtrate of dysentery patient feces melted by something, and further studied about this phenomenon. As a result, he identified bacteriophage independently, and named it as bacteriophage which means a bacteria killer. Since then, bacteriophages specifically acting against such pathogenic bacteria as *Shigella, Salmonella Typhi,* and *Vibrio cholerae* have been continuously identified.

Owing to the unique capability of bacteriophage to kill bacteria, bacteriophages have been studied and anticipated as a method to treat bacterial infections. However, after penicillin was found by Fleming, studies on bacteriophages had been only continued in some of Eastern European countries and the former Soviet Union because of the universalization of antibiotics. After the year of 2000, the merit of the conventional antibiotics faded because of the increase of antibiotic-resistant bacteria. So, bacteriophages are once again spotlighted as a new anti-bacterial agent that can replace the conventional antibiotics.

Furthermore, the recent regulation of using antibiotics is fortified by the government world-widely. The interest on bacteriophages is increasing more and also industrial applications are increasily achieved.

Therefore, the present inventors tried to develop a composition applicable for the prevention or treatment of enteropathogenic *E. coli* infections by using a bacteriophage that is isolated from the nature and can kill enteropathogenic *E. coli* selectively, and further to establish a method for preventing or treating the infections of enteropathogenic *E. coli* using the composition. As a result, the present inventors isolated bacteriophages suitable for this purpose and secured the nucleotide sequence of the genome that distinguishes the bacteriophage of the present invention from other bacteriophages. Then, we have developed a composition comprising the isolated bacteriophage as an active ingredient, and confirmed that this composition could be efficiently used for the prevention and treatment of enteropathogenic *E. coli* infections, leading to the completion of the present invention.

SUMMARY OF THE INVENTION

It is an object of the present invention to provide a Myoviridae bacteriophage Esc-CHP-2 that is isolated from the nature and can kill enteropathogenic *E. coli* specifically, which has the genome represented by the nucleotide sequence of SEQ. ID. NO: 1 (Accession NO: KCTC 12661BP).

It is another object of the present invention to provide a composition applicable for the prevention of enteropathogenic *E. coli* infections, which comprises the bacteriophage Esc-CHP-2 that can infect and kill enteropathogenic *E. coli*, as an active ingredient and a method for preventing the infections of enteropathogenic *E. coli* using said composition.

It is another object of the present invention to provide a composition applicable for the treatment of enteropathogenic *E. coli* infections, which comprises the bacteriophage Esc-CHP-2 that can infect and kill enteropathogenic *E. coli*, as an active ingredient and a method for treating the infections of enteropathogenic *E. coli* using said composition.

It is another object of the present invention to provide a disinfectant for preventing and treating the infections of enteropathogenic *E. coli* using said composition.

It is another object of the present invention to provide a drinking water additive for preventing and treating the infections of enteropathogenic *E. coli* using said composition.

It is also an object of the present invention to provide a feed additive effective upon farming by preventing and treating the infections of enteropathogenic *E. coli* using said composition.

To achieve the above objects, the present invention provides a Myoviridae bacteriophage ESC-CHP-2 that is isolated from the nature and can kill specifically enteropathogenic *E. coli*, which has the genome represented by the nucleotide sequence of SEQ. ID. NO: 1 (Accession NO: KCTC 12661BP), and a method for preventing and treating the infections of enteropathogenic *E. coli* using a composition comprising the bacteriophage as an active ingredient. The bacteriophage Esc-CHP-2 has been isolated by the present inventors and then deposited at Korean Collection for Type Cultures, Korea Research Institute of Bioscience and Biotechnology in Aug. 21, 2014 (Accession NO: KCTC 12661BP).

The present invention also provides a disinfectant, a drinking water additive, and a feed additive applicable for the prevention or treatment of enteropathogenic *E. coli* infections, which comprises the bacteriophage Esc-CHP-2 as an active ingredient.

Since the bacteriophage Esc-CHP-2 included in the composition of the present invention kills enteropathogenic *E. coli* efficiently, it is regarded as effective to prevent or treat *E. coli* diarrhea (infections) caused by enteropathogenic *E. coli*. Therefore, the composition of the present invention can be utilized for the prevention and treatment of *E. coli* diarrhea caused by enteropathogenic *E. coli*. In this specification, the *E. coli* diarrhea includes symptoms caused by the *E. coli* infections accompanying fever, diarrhea and the like.

In this description, the term "treatment" or "treat" indicates (i) to suppress the diarrhea caused by enteropathogenic *E. coli*; and (ii) to relieve the diarrhea caused by enteropathogenic *E. coli*.

In this description, the term "isolation" or "isolated" indicates all the actions to separate the bacteriophage by using diverse experimental techniques and to secure the characteristics that can distinguish this bacteriophage from others, and further includes the action of proliferating the bacteriophage via bioengineering techniques so as to make it useful.

The pharmaceutically acceptable carrier included in the composition of the present invention is the one that is generally used for the preparation of a pharmaceutical formulation, which is exemplified by lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but not always limited thereto. The composition of the present invention can additionally include lubricants, wetting agents, sweeteners, flavors, emulsifiers, suspending agents, and preservatives, in addition to the above ingredients.

In the composition of the present invention, the bacteriophage Esc-CHP-2 is included as an active ingredient. At this time, the bacteriophage Esc-CHP-2 is included at the concentration of $1\times10^1$ pfu/ml~$1\times10^{30}$ pfu/ml or $1\times10^1$ pfu/g~$1\times10^{30}$ pfu/g, and preferably at the concentration of $1\times10^4$ pfu/ml~$1\times10^{15}$ pfu/m or $1\times10^4$ pfu/g~$1\times10^{15}$ pfu/g.

The composition of the present invention can be formulated by the method that can be performed by those in the art by using a pharmaceutically acceptable carrier and/or excipient in the form of unit dose or in a multi-dose container. The formulation can be in the form of solution, suspension or emulsion in oil or water-soluble medium, extract, powder, granule, tablet or capsule. At this time, a dispersing agent or a stabilizer can be additionally included.

The composition of the present invention can be prepared as a disinfectant, a drinking water additive, or a feed additive according to the purpose of use, but not always limited thereto.

Advantageous Effect

The method for preventing and treating the infections of enteropathogenic *E. coli* using this composition comprising the bacteriophage Esc-CHP-2 as an active ingredient, have the advantage of high specificity to enteropathogenic *E. coli*, compared with the conventional methods based on the chemical materials including the conventional antibiotics. That means, the composition of the present invention can be used for preventing or treating the infections of enteropathogenic *E. coli* specifically without affecting other useful residential bacteria, and accordingly has fewer side effects. In general, when chemical materials such as antibiotics are used, the general residential bacteria are also damaged to weaken immunity in animals with carrying various side effects. In the meantime, the composition of the present invention uses the bacteriophage isolated from the nature as an active ingredient, so that it is very nature-friendly.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
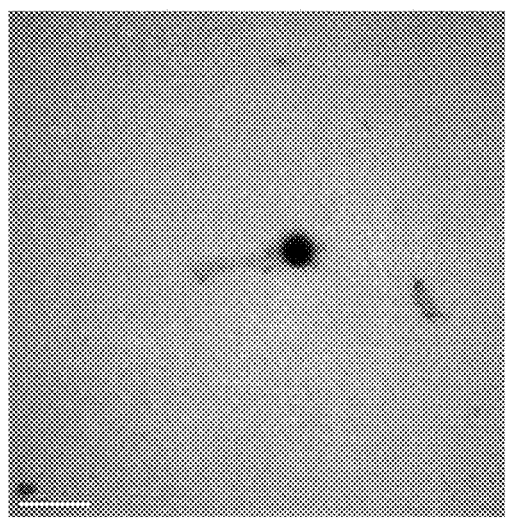
FIG. 1 is an electron micrograph showing the morphology of the bacteriophage Esc-CHP-2.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Isolation of Bacteriophage Capable of Killing Enteropathogenic *E. coli*

Samples were collected from the nature to screen the bacteriophage capable of killing enteropathogenic *E. coli*. The enteropathogenic *E. coli* used for the bacteriophage isolation herein were the one that had been isolated by the present inventors and identified as enteropathogenic *E. coli* previously.

The isolation procedure of the bacteriophage is described in detail hereinafter. The collected sample was added to the TSB (Tryptic Soy Broth) medium (pancreatic digest of casein, 17 g/L; papaic digest of soybean, 3 g/L; dextrose, 2.5 g/L; sodium chloride, 5 g/L; dipotassium phosphate, 2.5 g/L) inoculated with enteropathogenic *E. coli* at the ratio of 1/1000, followed by shaking culture at 37° C. for 3~4 hours. Upon completion of the culture, centrifugation was performed at 8,000 rpm for 20 minutes and supernatant was recovered. The recovered supernatant was inoculated with enteropathogenic *E. coli* at the ratio of 1/1000, followed by shaking culture at 37° C. for 3~4 hours. When the sample contained the bacteriophage, the above procedure was repeated total 5 times in order to increase the titer of the bacteriophage. After repeating the procedure 5 times, the culture solution proceeded to centrifugation at 8,000 rpm for 30 minutes and the resulting supernatant was recovered. The recovered supernatant was filtrated by using a 0.45 μm filter. The obtained filtrate was used in spot assay for examining whether or not the bacteriophage capable of killing enteropathogenic *E. coli* was included therein.

Spot assay was performed as follows; TSB medium was inoculated with enteropathogenic *E. coli* at the ratio of 1/1000, followed by shaking culture at 37° C. for overnight. 3 ml (1.5 of $OD_{600}$) of the culture broth of enteropathogenic *E. coli* prepared above was spread on the TSA (Tryptic Soy Agar; pancreatic digest of casein, 17 g/L; papaic digest of soybean, 3 g/L; sodium chloride, 5 g/L; agar, 15 g/L) plate. The plate stood in a chamber for about 30 minutes to dry. After drying, 10 μl of the resulting filtrate was spotted directly onto the surface of the enteropathogenic *E. coli* lawns and dried for about 30 minutes. Following drying, the plate was incubated at 37° C. for a day and then, examined for the formation of clear zones on the surface of the bacterial lawns. If a clear zone was generated where the filtrate was dropped, it could be judged that the bacteriophage capable of killing enteropathogenic *E. coli* was included in the filtrate. Through the above procedure, the filtrate containing the bacteriophage having the killing ability of enteropathogenic *E. coli* could be obtained.

After that, the bacteriophage was isolated from the filtrate confirmed above to have the bacteriophage capable of killing enteropathogenic *E. coli*. The conventional plaque assay was used for the isolation of pure bacteriophages. In detail, a plaque formed in the course of the plaque assay was picked up by using a sterilized tip, which was then added to the culture solution of enteropathogenic *E. coli*, followed by culturing at 37° C. for 4~5 hours. Upon completion of the culture, centrifugation was performed at 8,000 rpm for 20 minutes to obtain supernatant. The recovered supernatant was inoculated with enteropathogenic *E. coli* culture at the ratio of 1/50, followed by culturing at 37° C. for 4~5 hours. To increase the titer of the bacteriophage, the above procedure was repeated at least 5 times. Then, centrifugation was performed at 8,000 rpm for 20 minutes to obtain supernatant. Plaque assay was performed with the obtained supernatant. In general, the pure bacteriophage isolation is not completed by one-time procedure, so the above procedure was repeated by using the plague formed above. After at least 5 times of repeated procedure, the solution containing the pure bacteriophage was obtained. The procedure for the isolation of the pure bacteriophage was generally repeated until the generated plaques became similar in sizes and morphologies. And the final pure bacteriophage isolation was confirmed by the observation under electron microscope. Until the pure bacteriophage isolation was confirmed under electron microscope, the above procedure was repeated. The observation under electron microscope was performed by the conventional method. Briefly, the solution containing the pure bacteriophage was loaded on copper grid, followed by negative staining with 2% uranyl acetate. After drying thereof, the morphology was observed under transmission electron microscope. The electron micrograph of the bacteriophage isolated in the present invention is presented in FIG. 1. From the morphological observation, the bacteriophage isolated above was identified as belonging to the family Myoviridae.

The solution containing the pure bacteriophage confirmed above proceeded to purification. The culture broth of enteropathogenic *E. coli* was added to the solution containing the pure bacteriophage at the volume of 1/50 of the total volume of the bacteriophage solution, followed by culturing again for 4~5 hours. Upon completion of the culture, centrifugation was performed at 8,000 rpm for 20 minutes to obtain supernatant. This procedure was repeated 5 times to obtain a solution containing enough numbers of the bacteriophage. The supernatant obtained from the final centrifugation was filtered by a 0.45 μm filter, followed by the conventional polyethylene glycol (PEG) precipitation. Particularly, PEG and NaCl were added to 100 ml of the filtrate until reaching 10% PEG 8000/0.5 M NaCl, which stood at 4° C. for 2~3 hours. Then, centrifugation was performed at 8,000 rpm for 30 minutes to obtain the bacteriophage precipitate. The resulting bacteriophage precipitate was resuspended in 5 ml of buffer (10 mM Tris-HCl, 10 mM $MgSO_4$, 0.1% Gelatin, pH 8.0). This solution was called as the bacteriophage suspension or bacteriophage solution.

As a result, the pure bacteriophage purified above was collected, which was named as the bacteriophage Esc-CHP-2 and then deposited at Korean Collection for Type Cultures, Korea Research Institute of Bioscience and Biotechnology in Aug. 21, 2014 (Accession NO: KCTC 12661BP).

Example 2: Separation and Sequence Analysis of the Bacteriophage Esc-CHP-2 Genome The genome of the bacteriophage Esc-CHP-2 was separated as follows. The genome was separated from the bacteriophage suspension obtained in Example 1. First, in order to eliminate DNA and RNA of enteropathogenic *E. coli* included in the suspension, DNase I and RNase A were added 200 U each to 10 ml of the bacteriophage suspension, which was incubated at 37° C. for 30 minutes. 30 minutes later, to remove the DNase I and RNase A activity, 500 μl of 0.5 M ethylenediaminetetraacetic acid (EDTA) was added thereto, which was incubated for 10 minutes. The suspension was further incubated at 65° C. for 10 minutes and then added with 100 μl of proteinase K (20 mg/ml) to break the outer wall of the bacteriophage, followed by incubation at 37° C. for 20 minutes. After that, 500 µl of 10% sodium dodecyl sulfate (SDS) solution was added thereto, followed by incubation at 65° C. for 1 hour. 10 ml of the mixture of phenol:chloroform:isoamylalcohol in a ratio of 25:24:1 was added thereto, followed by mixing well. The mixture was centrifuged at 13,000 rpm for 15 minutes to separate each layer. The upper layer was obtained, to which isopropyl alcohol was added at the volume of 1.5 times the volume of the upper layer, followed by centrifugation at 13,000 rpm for 10 minutes to precipitate the genome of the bacteriophage. After collecting the precipitate, 70% ethanol was added to the precipitate, followed by centrifugation at 13,000 rpm for 10 minutes to wash the precipitate. The washed precipitate was recovered, vacuum-dried and then dissolved in 100 µl of water. This procedure was repeated to obtain a sufficient amount of the bacteriophage Esc-CHP-2 genome.

The nucleotide sequence of the genome of the bacteriophage Esc-CHP-2 obtained above was analyzed by Next Generation Sequencing (NGS) using illumina Mi-Seq device at National Instrumentation Center for Environmental Management, Seoul National University. As a result, it is suggested that the final genome of bacteriophage Esc-CHP-2 have 53,363 bp of size and the nucleotide sequence of the whole genome has SEQ. ID. NO: 1.

Similarity of the genomic sequence of the bacteriophage Esc-CHP-2 obtained above with the previously reported bacteriophage genome sequences was investigated by using BLAST. From the BLAST result, it is confirmed that the genomic sequence of the bacteriophage Esc-CHP-2 has a relatively high homology (91%) with the sequence of Enterobacteria bacteriophage phiEcoM-GJ1 (Genbank Accession NO: EF460875.1). However, the number of ORFs (Open Reading Frame) within the genome of bacteriophage Esc-CHP-2 was determined to 83 ORFs, while that of Enterobacteria bacteriophage phiEcoM-GJ1 was 75 ORFs.

Based upon this result, it is concluded that the bacteriophage Esc-CHP-2 should be a novel bacteriophage not reported previously.

Figure 2:
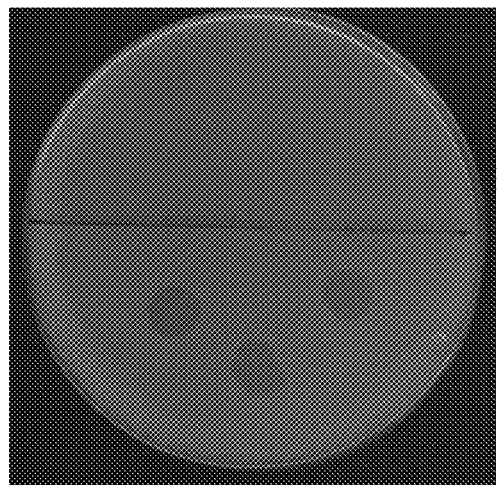
FIG. 2 is a photograph illustrating the capability of the bacteriophage Esc-CHP-2 to kill enteropathogenic *E. coli*. The clear zone on the dish is the formation of plaque by lysis of bacteria cells.

Example 3: Investigation of Killing Ability of the Bacteriophage Esc-CHP-2 Against Enteropathogenic E. Coli The killing ability of the isolated bacteriophage Esc-CHP-2 against enteropathogenic E. coli was investigated. To do so, the formation of clear zone was observed by the spot assay by the same manner as described in Example 1. The enteropathogenic E. coli used for this investigation were total 12 strains which had been isolated and identified as enteropathogenic E. coli previously by the present inventors. The bacteriophage Esc-CHP-2 demonstrated the killing ability against 9 strains of the enteropathogenic E. coli used in this experiment. The representative result of the killing ability test is shown in FIG. 2. In the meantime, the activity of the bacteriophage Esc-CHP-2 to kill *Staphylococcus aureus, Enterococcus faecalis, Enterococcus faecium, Lactobacillus plantarum, Streptococcus uberis* and *Pseudomonas aeruginosa* was also investigated. As a result, it is decided that the bacteriophage Esc-CHP-2 did not have the killing activity against these microorganisms.

Therefore, it was confirmed that the bacteriophage Esc-CHP-2 has the specific ability to kill enteropathogenic E. coli and a broad antibacterial spectrum against enteropathogenic E. coli, suggesting that the bacteriophage Esc-CHP-2 of the present invention could be used as an active ingredient of the composition for preventing and treating the infections of enteropathogenic E. coli.

Example 4: Preventive Effect of Bacteriophage Esc-CHP-2 on the Infections of Enteropathogenic E. coli 100 µl of the bacteriophage Esc-CHP-2 solution at $1\times10^8$ pfu/was added to a tube containing 9 ml of TSB. To another tube containing 9 ml of TSB, only the same volume of TSB was added. Then, the enteropathogenic E. coli culture was added to each tube to prepare bacterial suspension in 0.5 of $OD_{600}$. After that, the tubes were transferred to an incubator at 37° C., followed by shaking culture, during which the growth of enteropathogenic E. coli was observed. As presented in Table 1, the growth of enteropathogenic E. coli was inhibited in the tube added with the bacteriophage Esc-CHP-2 solution, while the growth of enteropathogenic E. coli was not inhibited in the tube without the bacteriophage Esc-CHP-2 solution.

TABLE 1

Inhibition of growth of enteropathogenic E. coli

| Item | $OD_{600}$ | | |
|---|---|---|---|
| | Culturing 0 min. | Culturing 60 min. | Culturing 120 min. |
| (−) bacteriophage solution | 0.5 | 1.3 | 1.9 |
| (+) bacteriophage solution | 0.5 | 0.3 | 0.2 |

The above results indicate that the bacteriophage Esc-CHP-2 not only inhibited the growth of enteropathogenic E. coli but also could kill them. Therefore, the bacteriophage Esc-CHP-2 can be used as an active ingredient of the composition for preventing the infections of enteropathogenic E. coli.

Example 5: Therapeutic Effect of Bacteriophage Esc-CHP-2 on the Infections of Enteropathogenic E. coli Therapeutic effect of the bacteriophage Esc-CHP-2 on animals affected by enteropathogenic E. coli was investigated. 4 weaning pigs at 25 days of age were grouped together; total 2 groups of pigs were raised in a pig pen (1.1 m×1.0 m) for 14 days. Heating system was furnished and the surrounding environment was controlled. The temperature and the humidity of the pig pen were controlled and the floor was cleaned every day. On the $7^{th}$ day of the experiment, all the animals were orally administered with 1 mL of enteropathogenic E. coli suspension using an oral injection tube. The enteropathogenic E. coli suspension administered above was prepared as follows: enteropathogenic E. coli was cultured in TSB medium at 37° C. for 18 hours and the bacterial cells were collected by centrifugation. Saline (pH 7.2) was added to the bacterial cell pellet to make cell suspension at a concentration of $10^9$ CFU/ml. From the next day of the enteropathogenic E. coli challenge, the experimental group (bacteriophage solution treated pigs) were orally administered with the bacteriophage Esc-CHP-2 ($10^9$ PFU/head) via the same way as used for the above administration twice a day. The control group (bacteriophage solution non-treated pigs) was treated with nothing. Feeds and drinking water were equally provided to both groups. After the challenge of enteropathogenic *E. coli*, all the animals were observed every day whether or not they experienced diarrhea. The observation was performed by measuring the diarrhea index. The diarrhea index was set as follows according to Fecal Consistency (FC) score (normal: 0, loose stool: 1, moderate diarrhea: 2, and severe diarrhea: 3). The results are shown in Table 2.

TABLE 2

Fecal Consistency score

| | Days after enteropathogenic *E. coli* challenge | | | | | | | |
|---|---|---|---|---|---|---|---|---|
| | 0 | 1 | 2 | 3 | 4 | 5 | 6 | 7 |
| Control group (− bacteriophage solution) | 2.25 | 2.75 | 2.5 | 2.5 | 2 | 2 | 1.5 | 1.5 |
| Experimental group (+ bacteriophage solution) | 2.25 | 2 | 1 | 0.5 | 0.5 | 0.25 | 0 | 0 |

From the above results, it is confirmed that the bacteriophage Esc-CHP-2 of the present invention could be very effective to treat the infections of enteropathogenic *E. coli*.

Example 6: Preparation of Feed Additives and Feeds

Feed additive containing bacteriophage Esc-CHP-2 at a concentration of $1 \times 10^8$ pfu/g was prepared using the bacteriophage Esc-CHP-2 solution. The preparation method thereof was as follows: Maltodextrin (40%, w/v) was added to the bacteriophage solution and then, trehalose was added to reach 10% of final concentration. After mixing well, the mixture was freeze-dried. Lastly, the dried mixture was grinded into fine powders. The drying process above can be replaced with vacuum-drying, drying at warm temperature, or drying at room temperature. To prepare the control feed additive for comparison, feed additive that did not contain the bacteriophage but contained buffer (10 mM Tris-HCl, 10 mM $MgSO_4$, 0.1% Gelatin, pH 8.0) only was prepared.

The above two kinds of feed additives were mixed with the 1,000 times volume of feed for pig farming respectively, resulting in two kinds of final feeds.

Example 7: Preparation of Drinking Water Additives and Disinfectants

Drinking water additive and disinfectant are different in intended use but same in the composition, so they have been prepared by the same manner. Drinking water additive (or disinfectant) containing bacteriophage Esc-CHP-2 at a concentration of $ix 10^8$ pfu/ml was prepared using the bacteriophage Esc-CHP-2 solution. Particularly, to prepare drinking water additive (or disinfectant), the bacteriophage ESC-CHP-2 solution was added to buffer solution to reach $1 \times 10^8$ pfu/ml, which was mixed well. For the comparison, the above buffer solution itself was used as the drinking water additive (or disinfectant) that did not contain the bacteriophage.

The prepared two kinds of drinking water additives (or disinfectants) were diluted in water at the ratio of 1:1000, and then used as drinking water or disinfectant.

Example 8: Effect on Pig Farming

The effect of the feeds, drinking water, and disinfectant prepared in Example 6 and Example 7 on pig farming was investigated. Particularly, the investigation was focused on diarrhea conditions by fecal consistency score used in Example 5. Total 30 piglets were grouped into three groups, and each group was composed of 10 piglets (group A: feed test group, group B: drinking water test group; and group C: disinfectant test group). The experiment was continued for 2 weeks. Each group was divided by two sub-groups comprising 5 piglets each. The sub-groups were divided according to the treatment of the bacteriophage Esc-CHP-2 or not (sub-group-①: treated with the bacteriophage Esc-CHP-2; and sub-group-②: not-treated with the bacteriophage). The piglets used in this experiment were weaning pigs at 20 days of age and raised in a separated room placed at a sufficient distance from each other. Each sub-group was divided and named as shown in Table 3.

TABLE 3

Sub-groups of pig farming experiment

| | Sub-group | |
|---|---|---|
| Item | Treated with the bacteriophage Esc-CHP-2 | Not-treated with the bacteriophage |
| Fed with feeds | A-① | A-② |
| Provided with drinking water | B-① | B-② |
| Treated with disinfectant | C-① | C-② |

Feeds were provided according to the conventional feed supply method as presented in Table 3 with the feeds prepared in Example 6. Drinking water was provided according to the conventional water supply method as presented in Table 3 with the drinking water prepared in Example 7. Disinfectant was treated three times a week with taking turns with the conventional disinfectant. That is, on the day when the disinfectant of the present invention was sprayed, the conventional disinfectant was not treated. The results are shown in Table 4.

TABLE 4

Fecal consistency score of pig farming experiment

| Group 그룹 | Fecal consistency score | | | | | | | | | | | | | |
|---|---|---|---|---|---|---|---|---|---|---|---|---|---|---|
| | d1 | d2 | d3 | d4 | d5 | d6 | d7 | d8 | d9 | d10 | d11 | d12 | d13 | d14 |
| A-① | 0.2 | 0 | 0 | 0.2 | 0 | 0 | 0 | 0 | 0.2 | 0 | 0.2 | 0 | 0 | 0 |
| A-② | 0 | 0 | 0.4 | 0.4 | 0.4 | 0.2 | 0.4 | 0.4 | 0.2 | 0.4 | 0.4 | 0.2 | 0.4 | 0.2 |
| B-① | 0 | 0.2 | 0 | 0 | 0.2 | 0 | 0.2 | 0 | 0 | 0 | 0.2 | 0 | 0 | 0 |
| B-② | 0.2 | 0 | 0.4 | 0.4 | 0.2 | 0.4 | 0.2 | 0.4 | 0.4 | 0.2 | 0.2 | 0.4 | 0.2 | 0.2 |
| C-① | 0 | 0.2 | 0 | 0 | 0.2 | 0 | 0 | 0.2 | 0 | 0 | 0 | 0.2 | 0 | 0 |
| C-② | 0.2 | 0 | 0.2 | 0.4 | 0.4 | 0.4 | 0.4 | 0.2 | 0.4 | 0.4 | 0.2 | 0.4 | 0.2 | 0.4 |

From the above results, it is confirmed that the feeds, drinking water, and the disinfectant prepared according to the present invention were effective in reducing the animal diarrhea. Therefore, it is concluded that the composition of the present invention could be efficiently applied for the improvement of productivity of animal farming.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for preventing or treating infections of enteropathogenic E. coli in a subject, the method comprising a step of administering to the subject a composition comprising Myoviridae bacteriophage Esc-CHP-2 (Accession NO: KCTC 12661BP) that is isolated from nature and can kill enteropathogenic E. coli specifically, which has the genome represented by the nucleotide sequence of SEQ ID NO: 1, as an active ingredient.

2. The method according to claim 1, wherein said composition is administered to the subject in the form of a feed additive, a drinking water additive, or a disinfectant.

* * * * *